(12) United States Patent
Kubo et al.

(10) Patent No.: US 9,226,646 B2
(45) Date of Patent: Jan. 5, 2016

(54) SUBSTRATE CONNECTING STRUCTURE

(71) Applicant: OLYMPUS CORPORATION, Tokyo (JP)

(72) Inventors: Takafumi Kubo, Akiruno (JP); Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/697,985

(22) Filed: Apr. 28, 2015

(65) Prior Publication Data

US 2015/0230693 A1 Aug. 20, 2015

Related U.S. Application Data

(63) Continuation of application No. PCT/JP2014/058468, filed on Mar. 26, 2014.

(30) Foreign Application Priority Data

Apr. 16, 2013 (JP) .................................. 2013-085766

(51) Int. Cl.
*A61B 1/00* (2006.01)
(52) U.S. Cl.
CPC .................................. *A61B 1/00124* (2013.01)
(58) Field of Classification Search
CPC ........... A61B 1/00124; A61B 1/00018; A61B 1/00114; H01R 9/0735; H01R 9/095; H01R 9/0515; H01R 9/091; H01R 12/51; H01R 12/53; H01R 12/57
USPC ................................................ 174/261, 72 A
See application file for complete search history.

(56) References Cited

U.S. PATENT DOCUMENTS

| | | | |
|---|---|---|---|
| 2002/0050386 A1* | 5/2002 | Aizawa | H01R 9/034 174/74 R |
| 2010/0231702 A1* | 9/2010 | Tsujimura | A61B 1/00096 348/65 |
| 2012/0197081 A1 | 8/2012 | Kimura | |
| 2013/0248222 A1* | 9/2013 | Inaba | A61B 1/00114 174/107 |

FOREIGN PATENT DOCUMENTS

| | | |
|---|---|---|
| EP | 2481341 A1 | 8/2012 |
| JP | 63-68128 A | 3/1988 |

(Continued)

OTHER PUBLICATIONS

International Search Report dated Jun. 24, 2014 issued in PCT/JP2014/058468.

*Primary Examiner* — Hoa C Nguyen
*Assistant Examiner* — Amol Patel
(74) *Attorney, Agent, or Firm* — Scully, Scott, Murphy & Presser, P.C.

(57) ABSTRACT

A substrate connecting structure includes a circuit substrate where an electrical component is installed on the back face, a signal cable into which a plurality of signal transmission lines electrically connected to first signal line connecting portions and to second signal line connecting portions, respectively, are inserted, and a coupling member that is formed by a conductive member including a fixing section disposed at the end portion of the signal cable, a flat section on the front face of the circuit substrate, and a through hole, the coupling member fixing the signal cable and the circuit substrate, wherein the central axis of the signal cable is displaced toward the back face side with respect to the central axis of the circuit substrate.

10 Claims, 18 Drawing Sheets

(56) References Cited

FOREIGN PATENT DOCUMENTS

| | | |
|---|---|---|
| JP | 2002-359447 A | 12/2002 |
| JP | 2008-237732 A | 10/2008 |
| JP | 2009-279148 A | 12/2009 |
| JP | 2011023319 A * | 2/2011 |
| JP | 2012-157472 A | 8/2012 |
| JP | 2012-221586 A | 11/2012 |

* cited by examiner

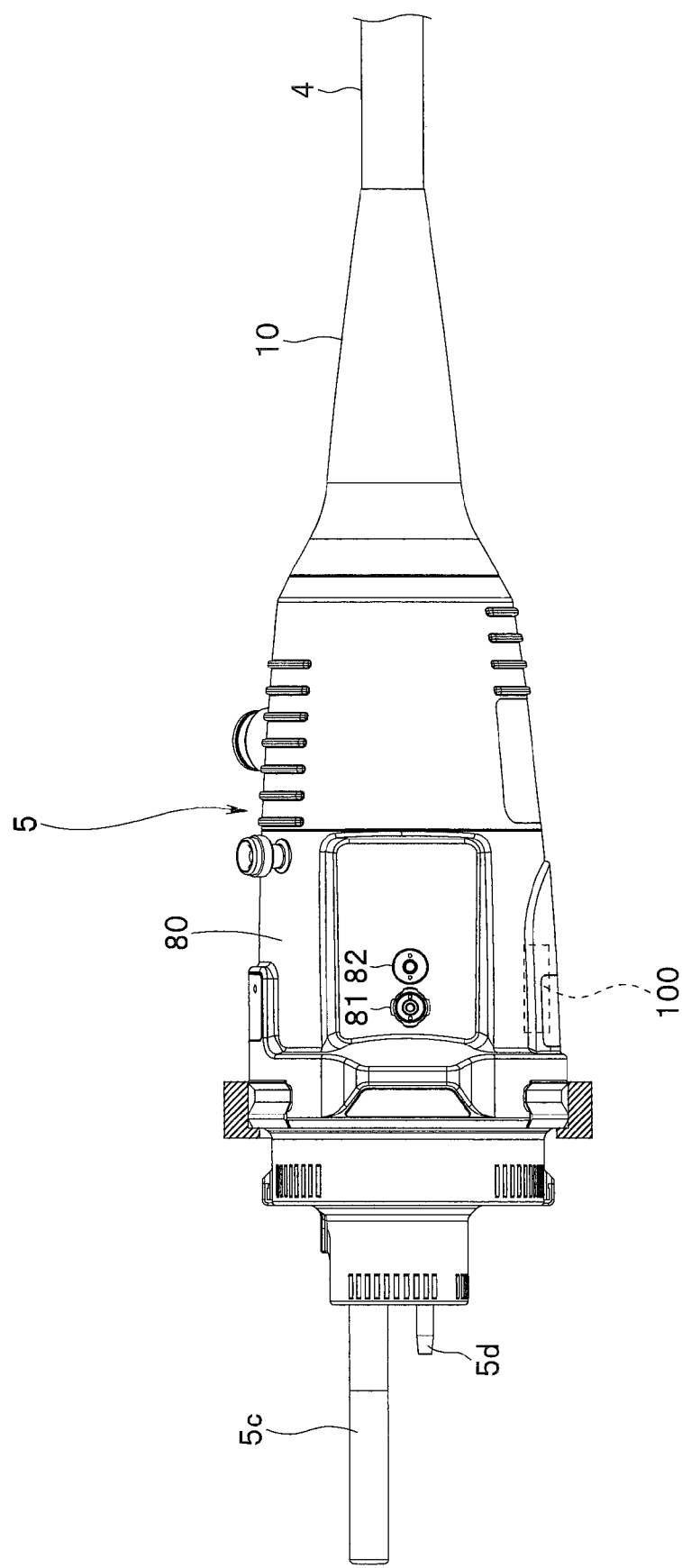

SUBSTRATE CONNECTING STRUCTURE

CROSS REFERENCE TO RELATED APPLICATION

This application is a continuation application of PCT/JP2014/058468 filed on Mar. 26, 2014 and claims benefit of Japanese Application No. 2013-085766 filed in Japan on Apr. 16, 2013, the entire contents of which are incorporated herein by this reference.

BACKGROUND OF THE INVENTION

1. Field of the Invention

The present invention relates to a substrate connecting structure between a plurality of signal lines inserted into a signal cable and a substrate to which the signal lines are electrically connected.

2. Description of the Related Art

Endoscopes are used in medical fields, industrial fields, and the like. The endoscopes include a so-called electronic endoscope, which incorporates an image pickup apparatus in a distal end portion of an insertion portion. There is a demand for electronic endoscopes for improving the quality of images, and thus high-resolution image pickup devices have been developed.

In an endoscope, a signal transmission channel, connecting an image pickup apparatus incorporated in the distal end portion of an insertion portion and an external device such as a video processor, has a long length. Additionally, in the insertion portion of the endoscope and the operation portion of the endoscope, a signal cable is inserted, as well as many endoscope built-in items such as a light guide fiber bundle that supplies illumination light, an air feeding tube forming an air feeding conduit, a water feeding tube forming a water feeding conduit, a multi-purpose tube serving both a suction conduit and a treatment instrument conduit, and a bending wire that brings a bending portion into bending action.

As to an electronic endoscope apparatus, it is possible to achieve the improvement of image quality and the reduction of the size of a signal cable to be inserted into an insertion portion by providing a relay circuit substrate that amplifies drive signals for an image pickup device in the operation portion of the endoscope. For example, Japanese Patent Application Laid-Open Publication No. 2009-279148 discloses an electronic endoscope apparatus that prevents itself from being increased in size, in particular prevents an insertion portion from being increased in diameter even when an image pickup apparatus capable of acquiring high-quality images is disposed in the distal end portion of the insertion portion.

The relay circuit substrate provided in the operation portion of the endoscope is configured to have a small size. In addition, a substrate-to-substrate connector to be detachably connected to the relay circuit substrate is also configured to have a small size. The substrate-to-substrate connector is provided in the end portion of a signal cable extended from the image pickup apparatus.

The substrate-to-substrate connector and the signal cable is inserted from one end side of the insertion portion, drawn out from the other end side, led into the operation portion, and connected to the relay circuit substrate. For this reason, it is desired to make a width dimension and a thickness dimension, which is the outside shape of the substrate-to-substrate connector as small as possible to allow the substrate-to-substrate connector to pass through the insertion portion smoothly. In addition, it is desired to design a configuration that prevents a break or the like from occurring owing to loads imposed on a joining portion between a signal line and the substrate in inserting work or in connector connecting/disconnecting work.

For example, Japanese Patent Application Laid-Open Publication No. 2012-221586 discloses a cable fixture that enables fixing a plurality of cables on the edge portion of a printed circuit substrate and positioning the plurality of cables with good precision and allows soldering the cables to a connecting pad of the printed circuit substrate to be performed easily with good workability.

SUMMARY OF THE INVENTION

A substrate connecting structure in one aspect of the present invention includes a circuit substrate including a front face and a back face opposite to the front face, where an electrical component is installed on the back face, a signal cable into which a plurality of signal transmission lines are inserted, the plurality of signal transmission lines being electrically connected to first signal line connecting portions provided at predetermined positions on the front face and to second signal line connecting portions provided at predetermined positions on the back face, respectively, and a coupling member that is formed by a conductive member including an annular fixing section disposed and fixed so as to cover and wrap the outer circumferential face of the cable end portion of the signal cable, a flat section joined and fixed to the front face of the circuit substrate, and a through hole that is provided between the flat section and the fixing section and communicates between one face and the other face of the coupling member, the coupling member integrally fixing the signal cable and the circuit substrate, wherein the cable central axis of the signal cable fixed to the fixing section is displaced toward the side of the back face with respect to the longitudinal direction central axis of the circuit substrate to which the flat section is fixed.

BRIEF DESCRIPTION OF THE DRAWINGS

FIG. 9A is a diagram illustrating the alignment of the coupling member and the element side substrate;

FIG. 9B is a diagram illustrating a coupling member joining step of joining the flat section of the coupling member to the joining plane of the element side substrate with solder;

FIG. 9C is a diagram illustrating a cable end portion fixing step of fixing the cable end portion of the first signal cable to the coupling member integrated with the element side substrate;

FIG. 9D is a diagram illustrating a step of connecting first-face-side signal lines among a plurality of signal lines to a first face of the element side substrate with which the coupling member is integrated;

FIG. 9E is a diagram illustrating a step of connecting second-face-side signal lines among the plurality of signal lines to a second face of the element side substrate with which the coupling member is integrated;

FIG. 15A is a diagram illustrating the endoscope connector including an RFID that can perform communication in two directions;

DETAILED DESCRIPTION OF THE PREFERRED EMBODIMENT

An embodiment of the present invention will be described below with reference to the drawings.

Figure 1:
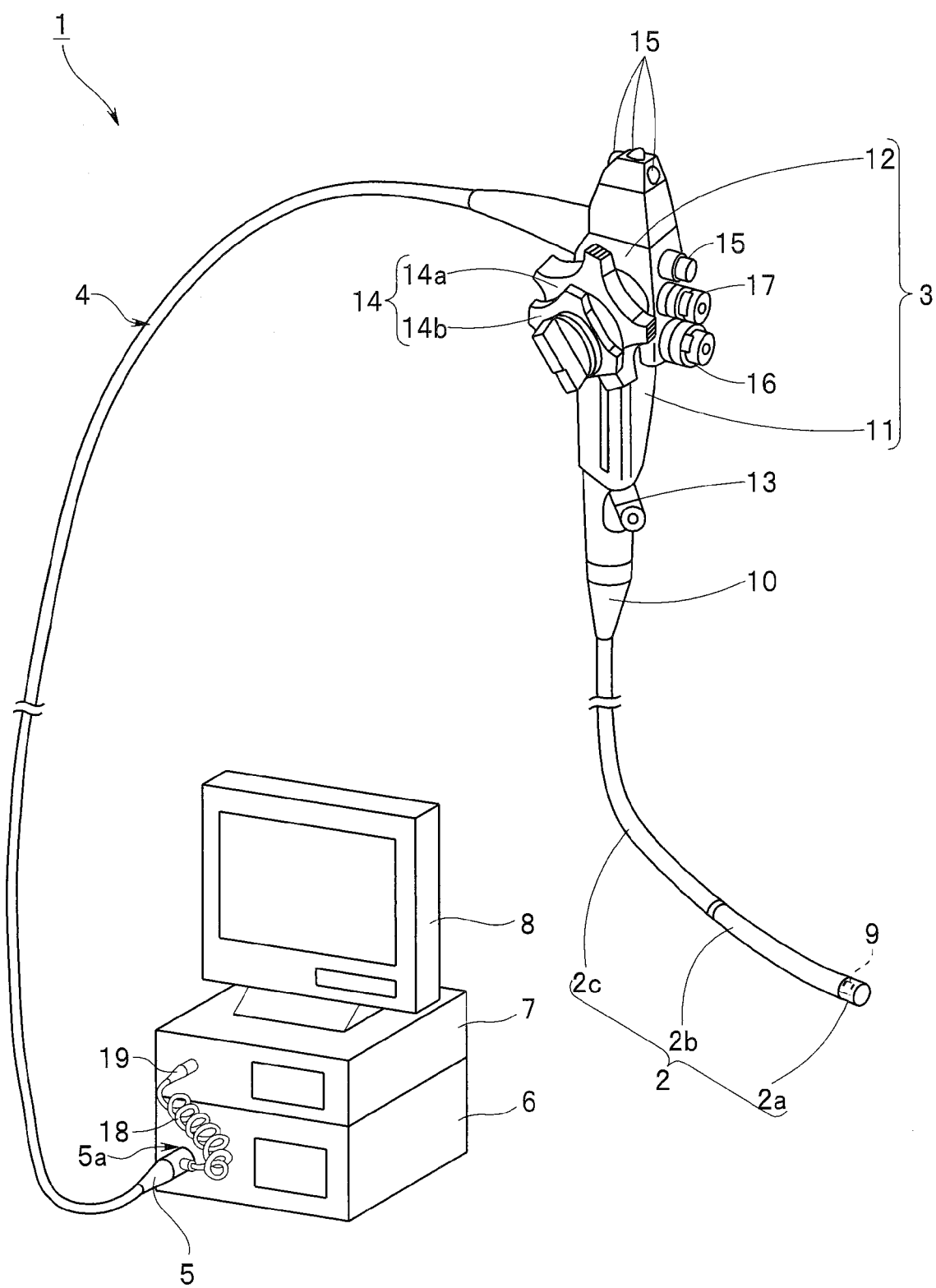
FIG. 1 is a diagram illustrating an endoscope including an image pickup apparatus module.

As shown in FIG. 1, an endoscope 1 includes an insertion portion 2, an operation portion 3, and a universal cable 4.

The universal cable 4 is provided with an endoscope connector 5 in the proximal end portion thereof. The endoscope connector 5 is detachably connected to, for example, a light source apparatus 6 being an external device. Reference numeral 7 denotes a video processor and reference numeral 8 denotes a color monitor.

The insertion portion 2 is an elongated long-length member that is to be inserted into a site to be observed. The insertion portion 2 is formed by coupling a distal end portion 2a, a bending portion 2b, and a flexible tube portion 2c in a coupled manner. The distal end portion 2a incorporates an illumination optical system including a light guide (not shown) and an image pickup apparatus 9 including an image pickup device such as a CCD and a C-MOS. The bending portion 2b is configured to be bent, for example, in four directions of upward, downward, leftward, and rightward directions. The flexible tube portion 2c is a long tubular member having flexibility.

The operation portion 3 is formed by combining a first exterior body 11 and a second exterior body 12. The first exterior body 11 is provided with, for example, a treatment instrument insertion opening 13. The distal end side of the first exterior body 11 is coupled and fixed to the proximal end portion of the insertion portion 2 integrally via a bend preventing member 10.

The second exterior body 12 is provided with a bending operation portion 14, various switches 15, an air/water feeding button 16, a suction button 17, and the like. The bending operation portion 14 is provided with, for example, bending operation knobs 14a and 14b for subjecting the bending portion 2b to bending operation. For example, rotating the bending operation knob 14a by a surgeon in a predetermined direction causes a bending wire, which is not shown, to be pulled or slackened, leading the bending portion 2b to perform bending action in the upward direction.

The various switches 15 is, for example, a release switch, a freeze switch, and an observation mode changing switch for changing over between normal observation and fluorescence observation.

Note that reference numeral 18 denotes an electric cable. The electric cable 18 is connected to the video processor 7 via a connector 19 for the processor.

Figure 2:
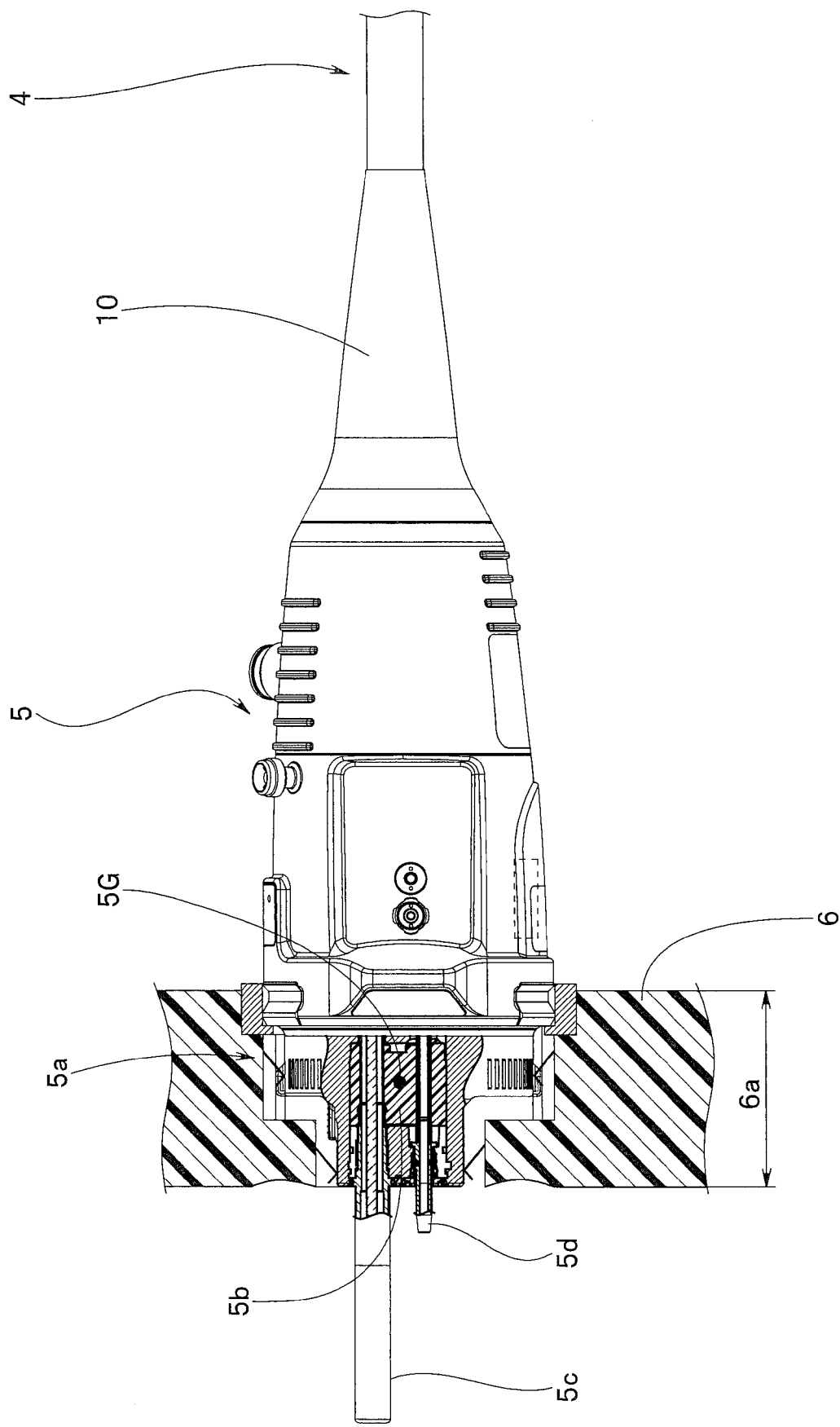
FIG. 2 is a diagram illustrating an endoscope connector subjected to balance adjustment.

The endoscope connector 5 is desired to be able to be mounted easily to the light source apparatus 6 and held in a straight line with stability. For this reason, in the endoscope connector 5, a balance adjustment member 5b is provided in an internal space, which is formed in a holding portion 5a of the endoscope connector 5 disposed in an endoscope held area 6a of the light source apparatus 6 shown in FIG. 2.

In the endoscope connector 5, a center of gravity 5G is positioned in the endoscope held area 6a, which prevents the connector 5 from inclining when the connector 5 is connected to the light source apparatus 6, enabling the reduction of force needed for mounting.

In addition, the center of gravity 5G positioned in the endoscope held area 6a in a mounted state makes the endoscope connector 5 held with respect to the light source apparatus 6 substantially horizontally with stability. As a result, for example, in a configuration in which a first contact 5h1 and a second contact 5h2 are provided on the outer circumferential face of the holding portion 5a as shown in FIG. 3, the contacts 5h1 and 5h2 provided in the holding portion 5a, and a contact provided in the endoscope held area 6a, which is not shown, are brought into a stable conducted state.

Furthermore, the water tightness of the endoscope connector 5 is also enhanced by hermetically sealing the balance adjustment member 5b in the internal space, for example, as a sealing member having insulation properties.

Reference character 5c denotes a light guide pipe sleeve, to which illumination light is incident. Reference character 5d is an air feeding pipe sleeve, to which gas is air fed.

Figure 3:
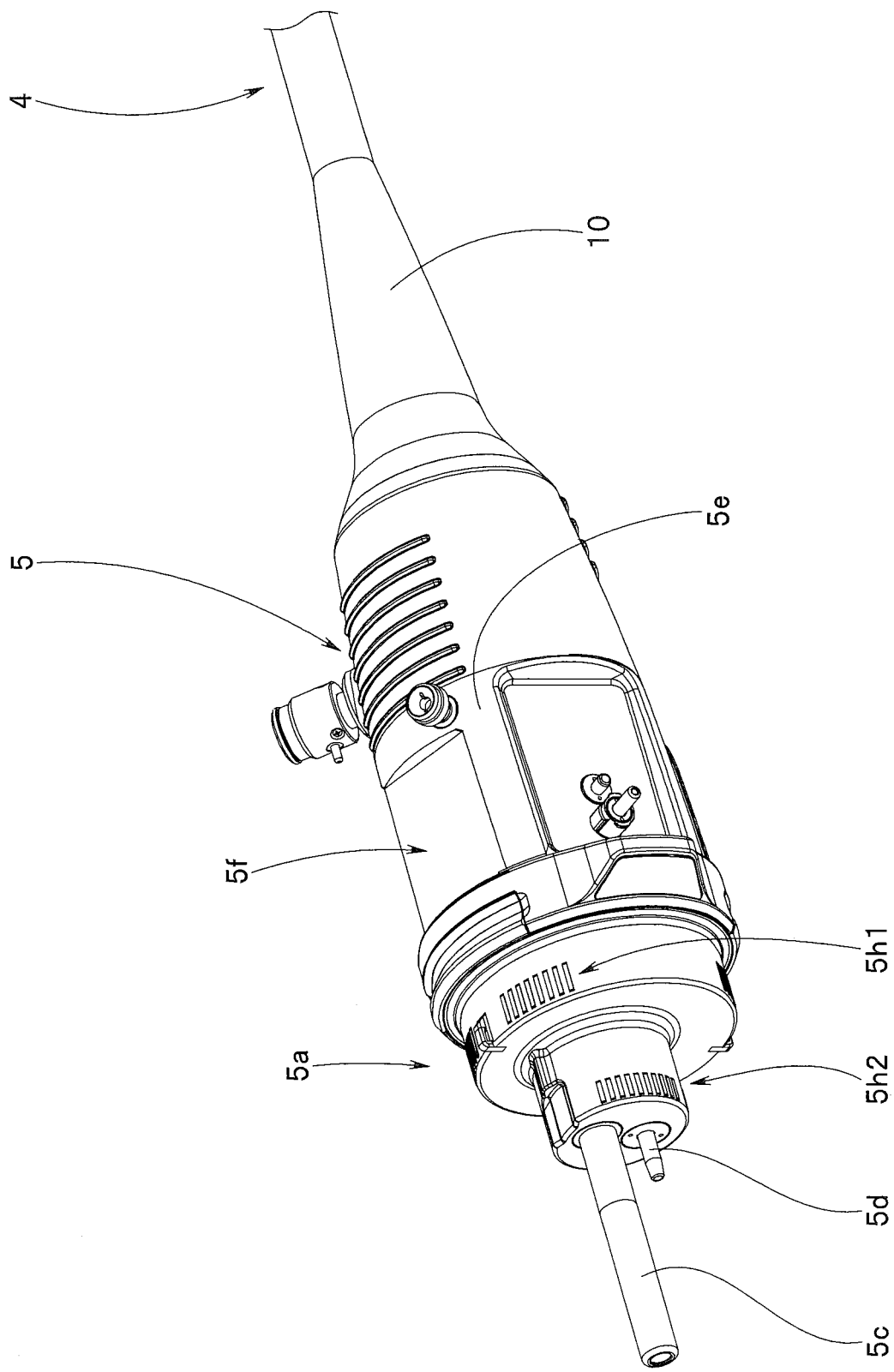
FIG. 3 is a diagram illustrating the endoscope connector including a display section.

Note that, as shown in FIG. 3, for example, a liquid crystal display monitor 5f may be provided, as a display device, at a predetermined position in an exterior portion 5e of the endoscope connector 5. The liquid crystal display monitor 5f is electrically connected to a storage element (not shown) incorporated in the connector 5, the storage element having a configuration that enables communication with an external apparatus in a wireless or wired manner, and the liquid crystal display monitor 5f has a screen on which various kinds of information and the like are displayed.

For example, in order to perform an endoscopic examination, connecting the endoscope connector 5 to the light source apparatus 6, connecting the endoscope connector 5 to the video processor 7, and bringing the power source into an on-state causes the liquid crystal display monitor 5f to display, for example, patient information, reprocess information, and the like. In contrast, when the surgeon uses the endoscope 1, the liquid crystal display monitor 5f displays endoscope internal information, operating information on the external apparatus connected to the endoscope, and the like. Accordingly, medical professionals can readily obtain various kinds of information.

Figure 4:
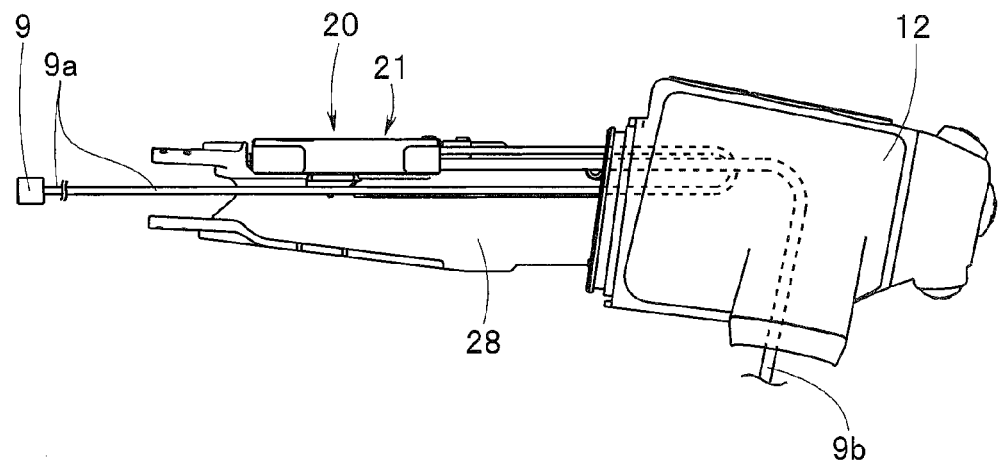
FIG. 4 is a diagram illustrating a relay unit provided in an operation portion.

As shown in FIG. 4, on the second exterior body 12 forming the operation portion 3, a ground plane 28 being an operation portion skeleton component is integrally fixed at a predetermined position. The ground plane 28 is made of, for example, stainless steel, and is a member for grounding. The ground plane 28 is formed such that various components to be provided in the operation portion 3 can be attached in an optimum state.

Reference numeral 20 denotes a relay unit. In a state that the relay unit 20 is attached and fixed to the ground plane 28, a first signal cable 9a and a second signal cable 9b enter the case from the proximal end face side of a housing case 21 forming the relay unit 20.

Figure 5:
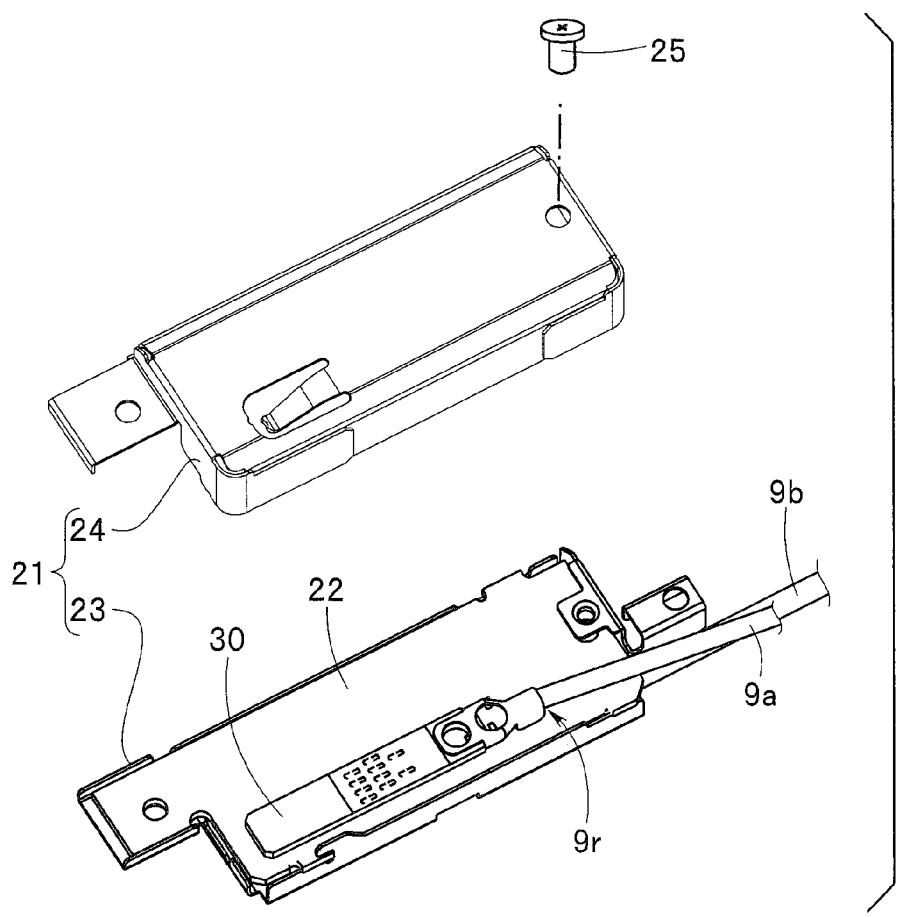
FIG. 5 is a diagram illustrating an element side substrate provided on a first signal cable accommodated in the case body of a housing case and a relay circuit substrate provided on a second signal cable.

As shown in FIG. 5, the second signal cable 9b is configured to have predetermined length dimension and diameter dimension. One end of the second signal cable 9b is connected to a relay circuit substrate 22 in the relay unit 20, and the other end is connected to a substrate in the endoscope connector 5, which is not shown.

The first signal cable 9a is a signal cable that is extended from the image pickup apparatus 9. The first signal cable 9a is configured to have predetermined length dimension and diameter dimension. In a cable end portion 9r of the first signal cable 9a, an element side substrate 30 is provided. The element side substrate 30 is a circuit substrate that is to be connected to the relay circuit substrate 22 in the relay unit 20.

The housing case 21 is formed by fixing a case body 23 and a lid body 24 integrally with a fixing screw 25. The housing case 21 is separated into, as shown in FIG. 5, the case body 23 and the lid body 24 by removing the fixing screw 25. In this separated state, the element side substrate 30 provided on the first signal cable 9a and the relay circuit substrate 22 to which the second signal cable 9b is connected can be housed in the internal space of the case body 23 while being electrically connected.

On the relay circuit substrate 22, a relay substrate side connector, which is not shown, is provided as a detachable connector. In contrast, on the element side substrate 30, an element side connector to be described below (hereafter, specified as a detachable connector, refer to reference numeral 34 in FIG. 6) is provided as a detachable connector. The relay circuit substrate 22 and the element side substrate 30 have configurations that are detachable via the detachable connectors.

Figure 6:
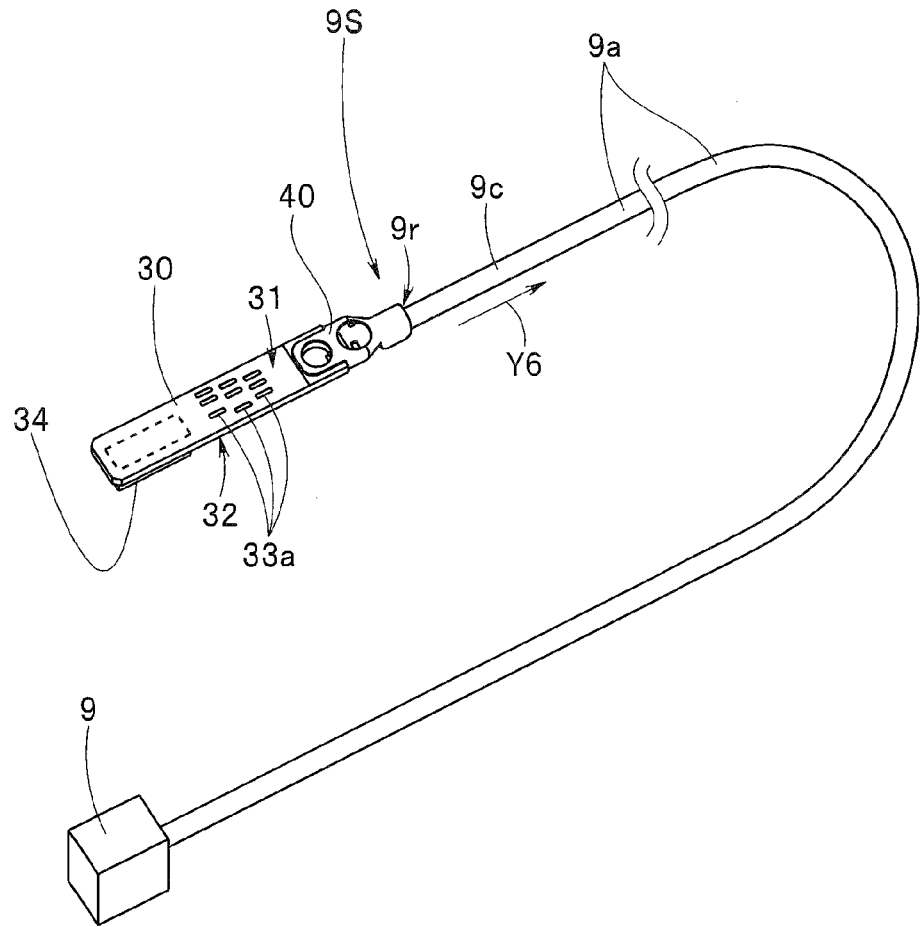
FIG. 6 is a diagram illustrating an image pickup apparatus module in which the first signal cable, the element side substrate, and a coupling member are integrally fixed.

As shown in FIG. 6, the image pickup apparatus module 9S is formed by providing the element side substrate 30 in the cable end portion 9r of the first signal cable 9a integrally with a coupling member 40 interposed therebetween. In the present embodiment, the first signal cable 9a is a cable formed by binding a plurality of signal lines being signal transmission lines into a bundle. The plurality of signal lines (reference numeral 47 in FIG. 8B, FIG. 9C, and the like) are covered with a covering sheath 9c.

Note that FIG. 6 does not show the signal lines extended from a cable end (not shown) of the first signal cable 9a.

Figure 7:
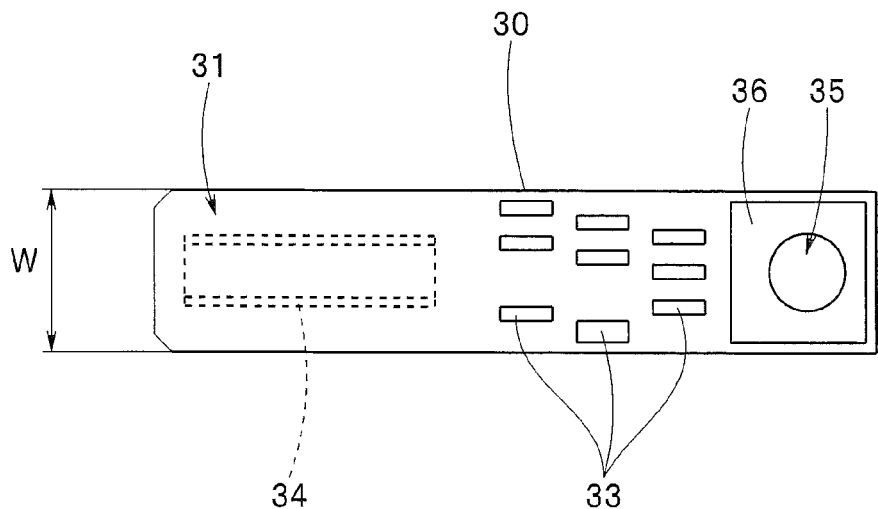
FIG. 7 is a diagram illustrating the configuration of the element side substrate.

As shown in FIG. 6 and FIG. 7, the element side substrate 30 has a first face 31, on the surface of which a plurality of first contacts 33a being first signal line connecting portions are included at predetermined positions, as an electric circuit. In addition, on the surface of a second face 32 being the opposite face of the first face 31, a plurality of second contacts being second signal line connecting portions (refer to reference character 33b in FIG. 9E) and a component connection portion (not shown) to which an electrical component is to be connected are provided at predetermined positions, as an electric circuit. In the component connection portion of the second face 32, for example, a detachable connector 34 is installed as the electrical component.

As shown in FIG. 7, the element side substrate 30 is set to have a predetermined width dimension, length dimension, and thickness dimension. At a predetermined position on the element side substrate 30, a bypass hole 35 having predetermined dimensions is formed. The bypass hole 35 is a through hole that communicates between the first face 31 and the second face 32. A width dimension W of the element side substrate 30 is set to be smaller than the inner diameter dimension of a hose (refer to reference character 2S in FIG. 11A or the like) forming the insertion portion 2 by a predetermined dimension.

The first face 31 of the element side substrate 30 includes, on the surface thereof, the plurality of first contacts 33a as well as a joining plane 36 forming a ground circuit. In the present embodiment, the joining plane 36 is formed such that a joining surface to be described below is disposed around the bypass hole 35 on the end face side that is on the proximal end face side of the element side substrate 30.

The joining plane 36 is joined and fixed to the joining surface of a flat section to be described below forming the coupling member 40 (reference numeral 41 in FIG. 8A and FIG. 8B) with solder for example. The ground circuit is formed as a plane ground, as an example.

Figure 8A:
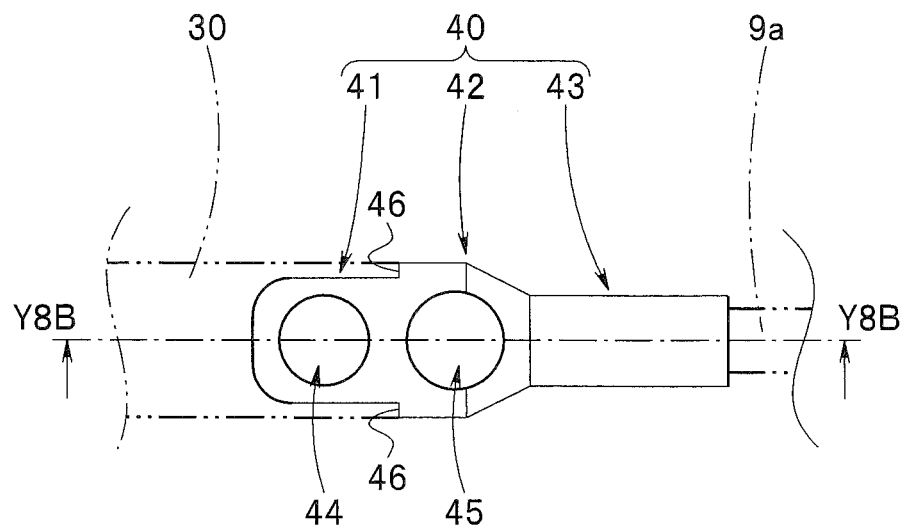
FIG. 8A is a plan view illustrating the configuration of the coupling member.

The coupling member 40 shown in FIG. 8A is formed into a predetermined shape, for example, with a metal member having conductivity. The coupling member 40 includes a flat section 41, a transition portion 42, and a fixing section 43 in an order from one end face side, and has a first through hole 44, and a second through hole 45. Reference numeral 46 denotes a contact portion, and the contact portion 46 is in contact with the proximal end face of the element side substrate 30.

Figure 8B:
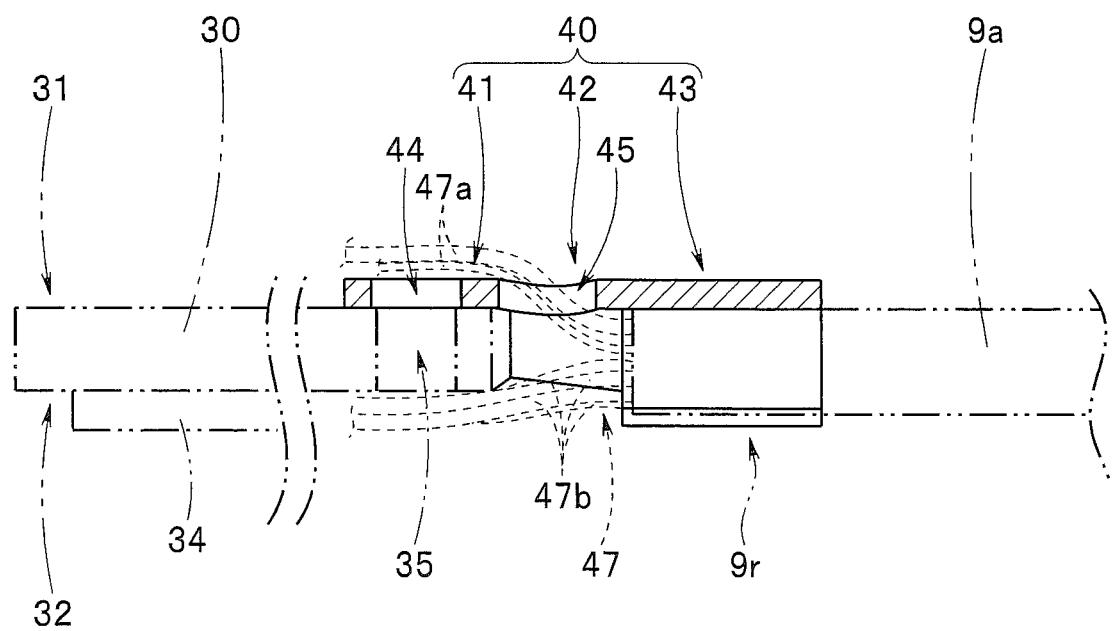
FIG. 8B is a cross sectional view taken along the line Y8B-Y8B of FIG. 8A, being a cross sectional view in a longitudinal-direction illustrating the configuration of the coupling member.

As shown in FIG. 8B, the flat section 41 is fixed integrally to the proximal end side of the element side substrate 30, which is shown by chain double-dashed lines. The fixing section 43 is fixed integrally to the cable end portion 9r of the first signal cable 9a, which is shown by chain double-dashed lines. That is, the element side substrate 30 and the first signal cable 9a are fixed integrally by the coupling member 40.

The flat section 41 shown in FIG. 8A and FIG. 8B has an eaves-like shape. One face side of the flat section 41 is formed as the joining surface disposed on the joining plane 36. The flat section 41 is joined and fixed to the joining plane 36 with solder, for example.

The first through hole 44 is a joining hole (hereafter, also described as a joining hole 44). The joining hole 44 communicates between the one face side of the flat section 41 and the other face side being an opposite face of the one face side. The diameter dimension of the joining hole 44 is set at a predetermined dimension and set to have a diameter larger than the diameter dimension of the bypass hole 35.

The fixing section 43 is an annular portion and is formed into, for example, a C shape. An inner circumferential face, which is one face side of the fixing section 43, is disposed so as to cover and wrap the outer circumferential face of the cable end portion 9r of the first signal cable 9a. The fixing section 43 is attached and fixed integrally to the cable end portion 9r of the first signal cable 9a by, for example, providing a crimp.

The second through hole 45 is a signal line insertion hole (hereafter, also described as a signal line insertion hole 45). The signal line insertion hole 45 communicates between one face side of the transition portion 42 and the other face side. The diameter dimension of the signal line insertion hole 45 is set at a predetermined dimension.

In the transition portion 42, the contact portion 46 is formed. Disposing the proximal end face of the element side substrate 30 being in contact with the contact portion 46 causes the joining hole 44 and the bypass hole 35 to be disposed almost concentrically, and the signal line insertion hole 45 is disposed at a predetermined position on the proximal end face side of the element side substrate 30.

Note that, in the signal line insertion hole 45, predetermined one or a number of signal lines out of a plurality of signal lines 47 extended from the cable end of the first signal cable 9a are inserted. Alternatively, a portion of the signal line insertion hole 45 may be configured to reach the flat section 41.

Referring to FIG. 9A to FIG. 9E, an assembly procedure to fix the first signal cable 9a and the element side substrate 30 integrally with the coupling member 40 to form the image pickup apparatus module 9S will be described.

To configure the image pickup apparatus module 9S, an operator prepares the first signal cable 9a, the element side substrate 30, and the coupling member 40. In addition, the operator prepares a soldering iron, solder, a crimping jig, and the like.

Note that, from the cable end portion 9r of the first signal cable 9a extended from the image pickup apparatus 9, the plurality of signal lines 47 and the cable general shield 9s are bared. The bared cable general shield 9s is gathered at the cable end portion 9r of the first signal cable 9a (refer to FIG. 9C).

In addition, on the second face 32 of the element side substrate 30, the detachable connector 34 having a predetermined width dimension, length dimension, and thickness dimension is installed.

Figure 9A:
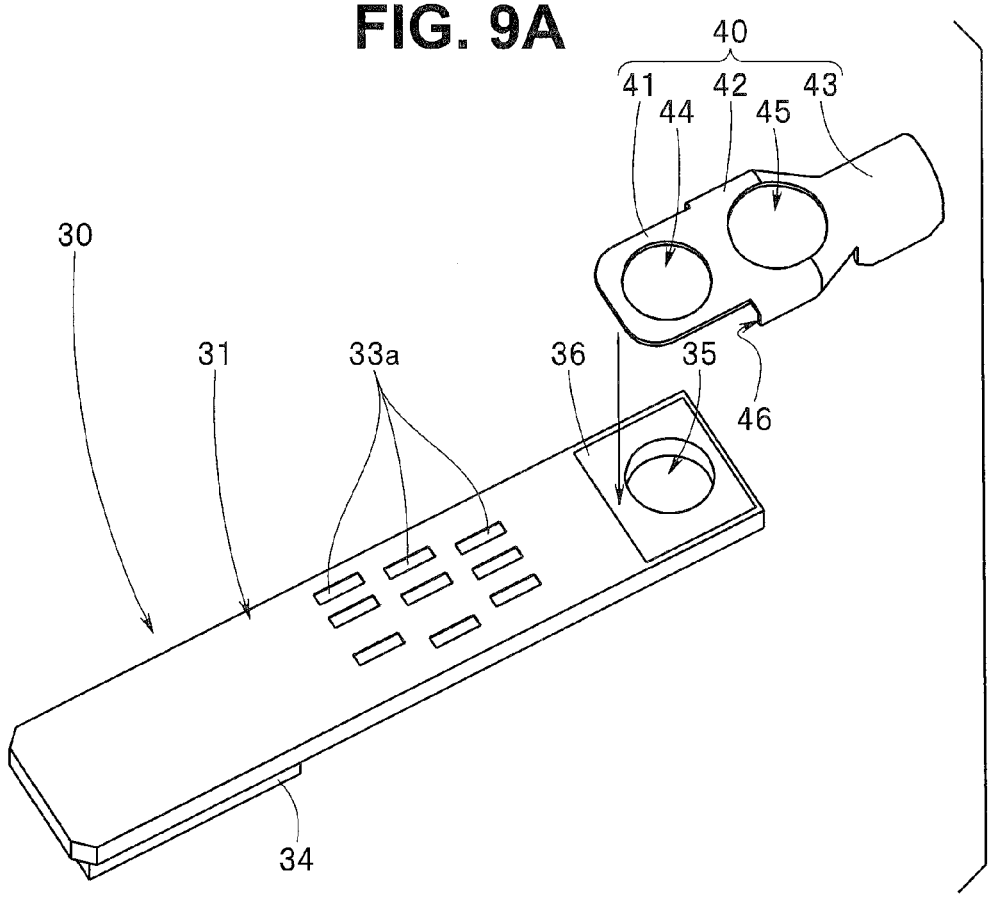
FIG. 9A to FIG. 9E are diagrams illustrating a procedure to fix the first signal cable and the element side substrate integrally with the coupling member.

First, an operator integrates the coupling member 40 and the element side substrate 30. At this point, the operator causes the joining surface of the flat section 41 forming the coupling member 40 to face the joining plane 36 of the element side substrate 30, as shown in FIG. 9A. The operator then brings the contact portion 46 in contact with the proximal end face of the element side substrate 30 and disposes the joining surface of the flat section 41 on the joining plane 36. The joining hole 44 and the bypass hole 35 are thereby disposed concentrically.

Figure 9B:
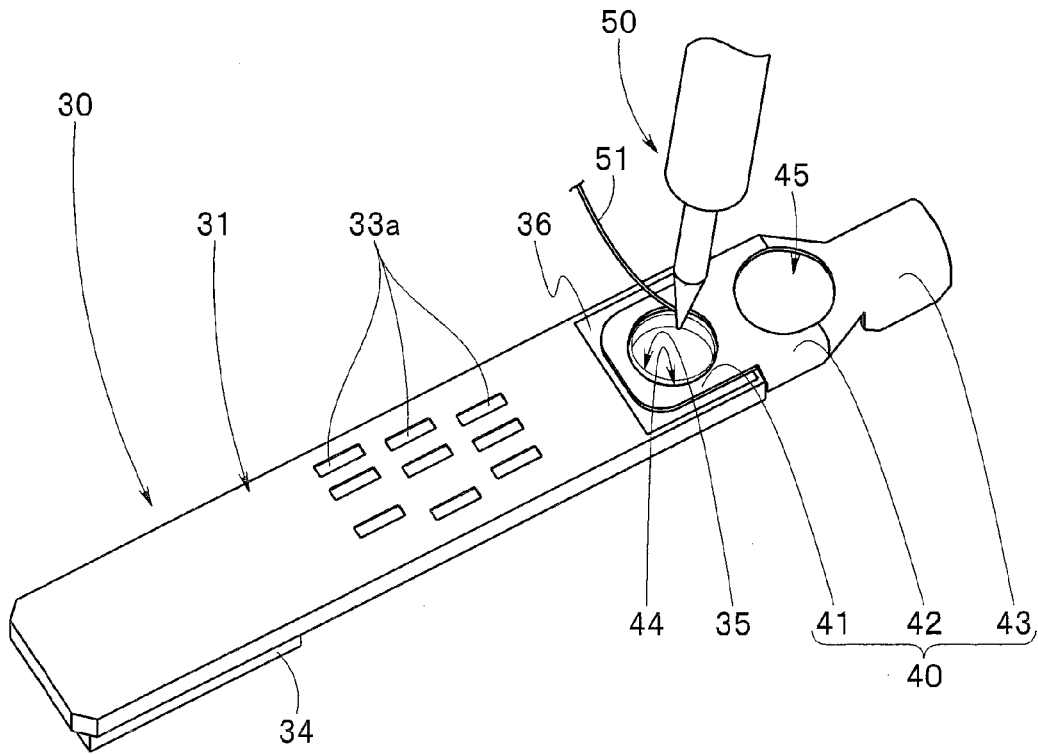

Next, the operator proceeds to a coupling member joining step. The coupling member joining step is work to fix the coupling member 40 to the first face 31 of the element side substrate 30 integrally. The operator melts solder 51 with a soldering iron 50 and supplies the molten solder 51 from the surrounding area of the bypass hole 35 via a gap between the bypass hole 35 and the joining hole 44 to the joining surface of the flat section 41 and the joining plane 36, as shown in FIG. 9B. As a result, the coupling member 40 is joined and fixed firmly to the element side substrate 30 by the solder 51.

Figure 9C:
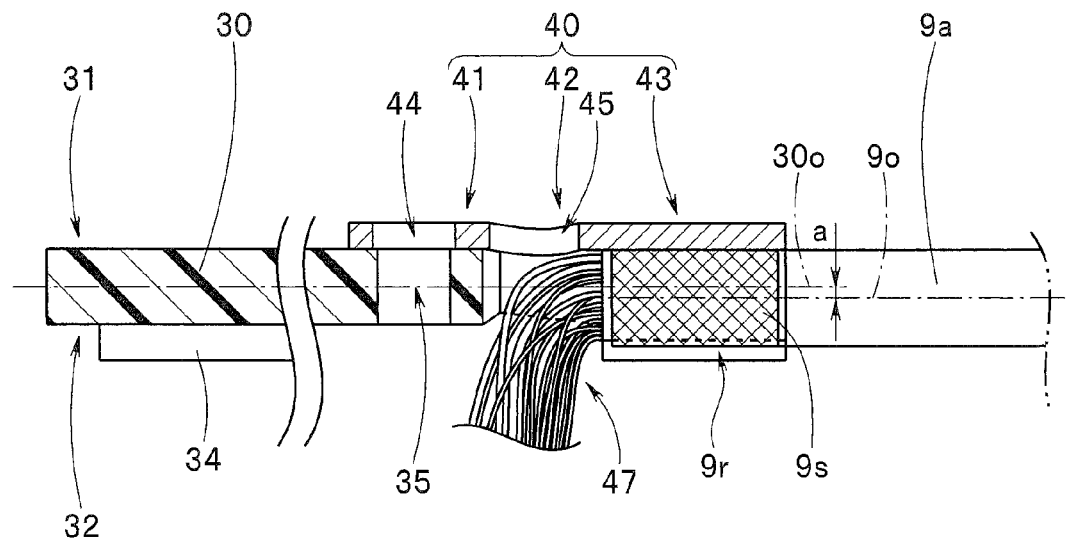

Next, the operator proceeds to a cable end portion fixing step. The cable end portion fixing step is work to integrally fix the cable end portion 9r of the first signal cable 9a to the fixing section 43 of the coupling member 40 that is integrally joined to the element side substrate 30. The operator disposes the cable end portion 9r of the first signal cable 9a, at which the cable general shield 9s is gathered, inside the inner circumferential face of the annular fixing section 43, as shown in FIG. 9C.

The operator afterward integrally fixes the cable end portion 9r to the fixing section 43 of the coupling member 40. At this point, the operator provides a crimp to the fixing section 43 that covers and wraps the cable end portion 9r with the crimping jig. As a result, the first signal cable 9a and the coupling member 40 integrally joined to the element side substrate 30 are brought into an integrally fixed state.

Figure 10A:
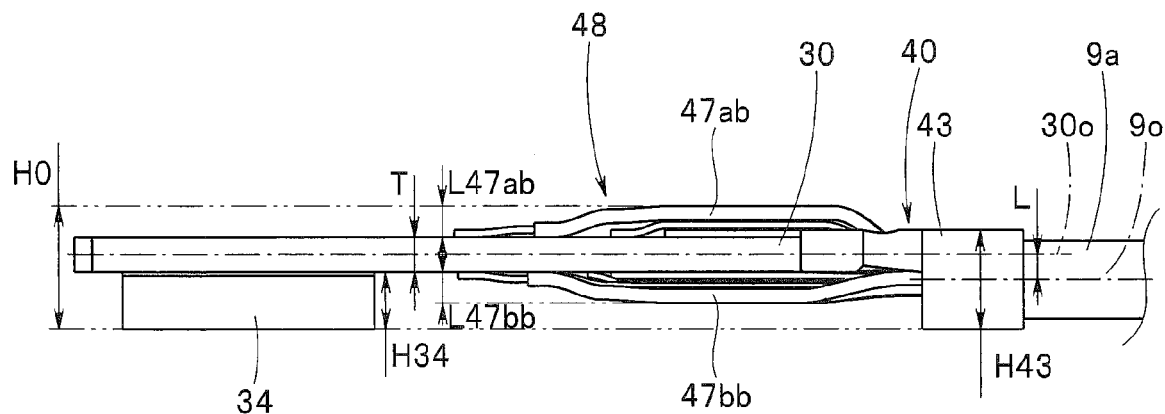
FIG. 10A is a diagram illustrating a maximum height dimension when the substrate longitudinal direction central axis of the element side substrate is disposed being displaced from the cable central axis of the first signal cable.

Note that, in this integrally fixed state, a cable central axis 90 of the first signal cable 9a is disposed being displaced (decentered) by a distance L toward the side of the detachable connector 34 installed on the second face 32 with respect to a substrate longitudinal direction central axis 30o of the element side substrate 30 fixed to the flat section 41, as shown in FIG. 10A. The plurality of signal lines 47 extended from the cable end of the first signal cable 9a are positioned on the side of the second face 32 on which the detachable connector 34 is installed.

The cable general shield 9s of the first signal cable 9a and the joining plane 36 forming the ground circuit of the element side substrate 30 are in a conducted state by way of the coupling member 40.

After fixing the cable end portion 9r to the fixing section 43, the operator proceeds to a signal line connecting step. The signal line connecting step is work to connect the plurality of signal lines 47 respectively to first contacts 33a of the first face 31 and second contacts 33b of the second face 32. The operator first separates the plurality of signal lines 47 into first-face-side signal lines 47a and second-face-side signal lines 47b. That is, the operator draws out and disposes the first-face-side signal lines 47a, which are a portion of the plurality of signal lines 47 and to be connected to the first contacts 33a of the first face 31, on the side of the first face 31 of the element side substrate 30 through the signal line insertion hole 45.

Next, the operator adjusts the lengths of the first-face-side signal lines 47a drawn out on the side of the first face 31 and adjusts the lengths of the second-face-side signal lines 47b positioned on the side of the second face 32.

Figure 9D:
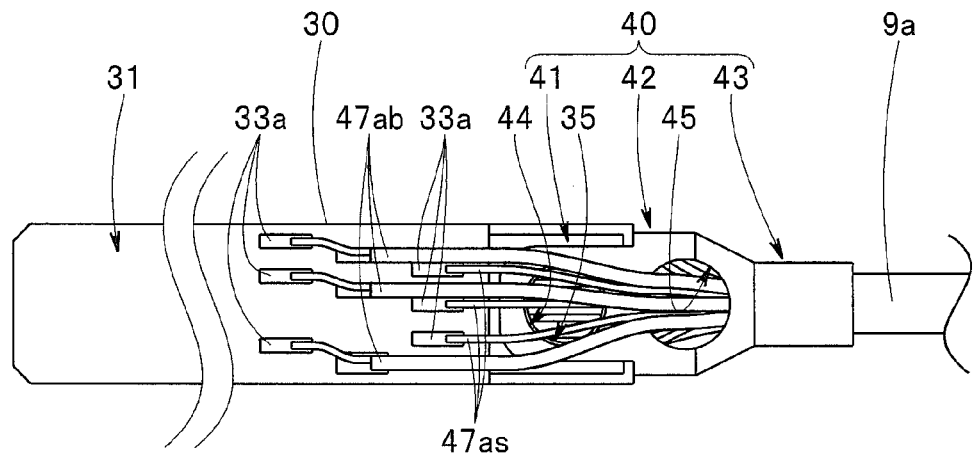

The operator afterward joins first-face-side small-diameter signal lines 47as that have a small diameter dimension among the first-face-side signal lines 47a to the first contacts 33a that are positioned at predetermined positions in proximity to the signal line insertion hole 45, as shown in FIG. 9D. In addition, the operator joins first-face-side large-diameter signal lines 47ab that have a large diameter dimension to the first contacts 33a that are positioned at predetermined positions away from the signal line insertion hole 45.

Figure 9E:
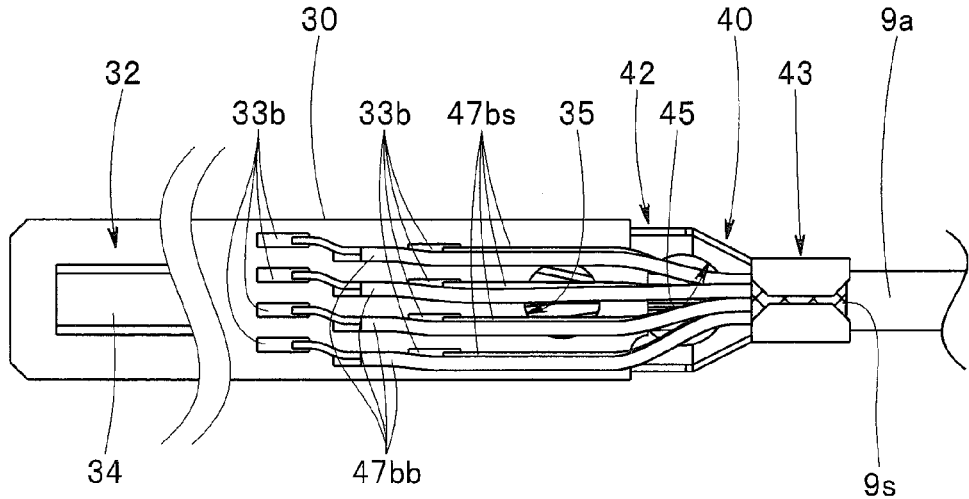

Next, the operator joins second-face-side small-diameter signal lines 47bs that have a small diameter dimension among second-face-side signal lines 47b to the second contacts 33b that are positioned at predetermined positions in proximity to the signal line insertion hole 45, as shown in FIG. 9E. In addition, the operator joins second-face-side large-diameter signal lines 47bb that have a large diameter dimension to the second contacts 33b that are positioned at predetermined positions away from the signal line insertion hole 45.

The assembly work is then completed by completing the work to connect all the signal lines 47a and 47b to all the contacts 33a and 33b. That is, the image pickup apparatus module 9S shown in FIG. 6 is formed.

As seen from the above, the coupling member 40 is formed by providing the flat section 41 having an eaves-like shape, the transition portion 42 having the signal line insertion hole 45, and the annular fixing section 43. The image pickup apparatus module is then formed by integrally fixing the cable end portion 9r of the first signal cable 9a on the fixing section 43 through crimping, and joining and fixing the joining plane 36 provided on the first face 31 of the element side substrate 30 on the joining surface of the flat section 41 with the solder.

The configuration allows a predetermined number of signal lines 47 that are a portion of the plurality of signal lines 47 that are bared from the cable end portion 9r of the first signal cable 9a to the side of the second face 32 to be drawn out to the side of the first face 31 through the signal line insertion hole 45. As a result, the plurality of signal lines 47 can be readily separated into the first-face-side signal lines 47a to be connected to the first contacts 33a of the first face 31 and the second-face-side signal lines 47b to be connected to the second contacts 33b of the second face 32.

Then, after separating the plurality of signal lines 47 for the two faces, it is possible to connect the individual first-face-side signal lines 47a to the respective first contacts 33a, and connect the individual second-face-side signal lines 47b to the respective second contacts 33b. Accordingly, the connecting workability in connecting the individual signal lines to the respective contacts can be significantly increased.

In addition, as described above, the element side substrate 30 is integrally fixed to the cable end portion 9r of the first signal cable 9a with the coupling member 40 interposed therebetween. As a result, it can be ensured to prevent loads from being applied to the first-face-side signal lines 47a connected to the first contacts 33a and the second-face-side signal lines 47b connected to the second contacts 33b when tension that pulls the first signal cable 9a toward the image pickup apparatus 9 acts on the cable 9a (refer to an arrow Y6 in FIG. 6).

Accordingly, loads are not applied to the joined portions between the respective first-face-side signal lines 47a and the respective first contacts 33a, and the joined portions between the respective second-face-side signal lines 47b and the respective second contacts 33b, either, which prevents the joined portions from being broken owing to tension acting on the signal cable.

In addition, the employed configuration is one in which small-diameter signal lines 47as and 47bs are joined to the contacts 33a and 33b in proximity to the signal line insertion hole 45, and the large-diameter signal lines 47ab and 47bb are joined to the contacts 33a and 33b at the positions away from the signal line insertion hole 45. As a result, it is possible to prevent a height dimension H from increasing by disposing the small-diameter signal lines 47as and 47bs between the substrate surface and the outer circumferential faces of the large-diameter signal lines 47ab and 47bb. In other words, the height dimension H is prevented from increasing by disposing the signal lines 47as and 47bs having a small diameter on the outside of the large-diameter signal lines 47ab and 47bb.

Additionally, the joined portions between the signal lines and the contacts are prevented from being broken owing to the tension acting on the cable. As a result, it is possible to dispose the first-face-side large-diameter signal lines 47ab and the second-face-side large-diameter signal lines 47bb closely along the first face 31 and the second face 32, respectively without slackening the first-face-side large-diameter signal lines 47ab and the second-face-side large-diameter signal lines 47bb in advance.

Accordingly, a distance L47ab from the substrate longitudinal direction central axis 30o to the first-face-side large-diameter signal lines 47ab and a distance L47bb from the substrate longitudinal direction central axis 30o to the second-face-side large-diameter signal lines 47bb are prevented from increasing owing to the respective large-diameter signal lines 47ab and 47bb being slackened, as shown in FIG. 10A.

In addition, after the cable general shield 9s is gathered at the cable end portion 9r of the first signal cable 9a, the fixing section 43 of the coupling member 40 is fixed to the cable end portion 9r, and the joining plane 36 of the element side substrate 30 and the joining surface of the flat section 41 of the coupling member 40 are joined with the solder. As a result, it can be ensured to secure a ground between the element side substrate 30 and the cable general shield 9s of the first signal cable 9a.

In a coupled portion 48 shown in FIG. 10A, the cable end portion 9r of the first signal cable 9a is integrally fixed to the fixing section 43 of the coupling member 40 in the state that the substrate longitudinal direction central axis 30o of the element side substrate 30 is displaced from the cable central axis 90 of the first signal cable 9a by the distance L. Additionally, the joining plane 36 provided on the first face 31 of the element side substrate 30 is joined and fixed to the joining surface of the flat section 41 of the coupling member 40 with the solder. As a result, a maximum height dimension H0 of the coupled portion 48, which is a distance from the outermost portion of the first-face-side large-diameter signal lines 47*ab* to the outermost portion of the detachable connector 34, can be expressed as $H0=L47ab+T+H34.$ In the above-described equation, T denotes the thickness of the element side substrate 30, and H34 denotes the height of the detachable connector 34, that is, a distance from the second face 32 of the element side substrate 30 to the outside of the detachable connector 34.

Note that, in FIG. 10A, a distance from the substrate longitudinal direction central axis 30*o* of the element side substrate 30 to the outermost portion of the detachable connector 34 and a distance from the substrate longitudinal direction central axis 30*o* of the element side substrate 30 to the outermost portion on the second face side of the fixing section 43 have the same dimension.

In addition, the following relationship is specified between the distance L47*ab* from the first face 31 of the element side substrate 30 to the outside of the first-face-side large-diameter signal lines 47*ab* and the external dimensions H43 of the fixing section 43 of the coupling member 40.

$L47ab<H43/2-T/2$

Figure 10B:
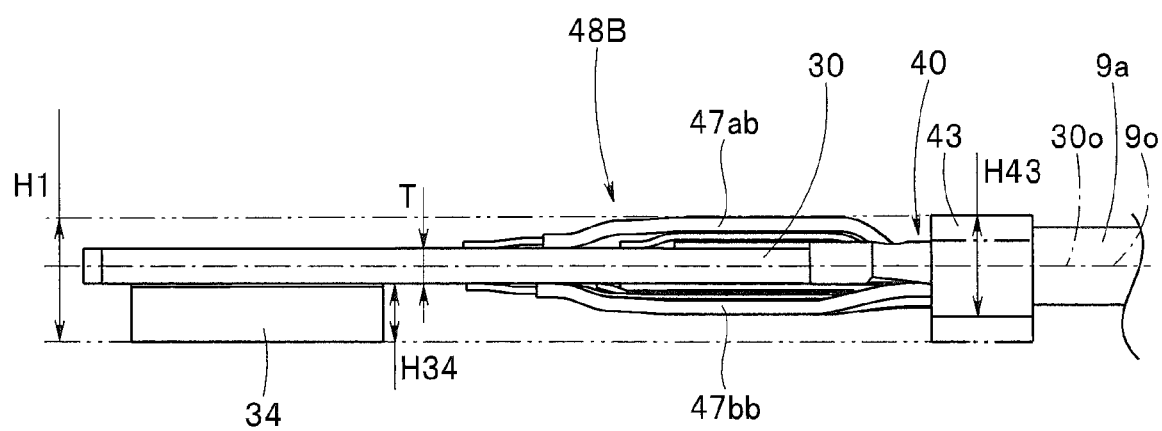
FIG. 10B is a diagram illustrating the maximum height dimension when the substrate longitudinal direction central axis of the element side substrate is matched to the cable central axis of the first signal cable.

In a coupled portion 48B shown in FIG. 10B, in the state that the substrate longitudinal direction central axis 30*o* of the element side substrate 30 is matched with the cable central axis 90 of the first signal cable 9*a*, the cable end portion 9*r* of the first signal cable 9*a* is integrally fixed to the fixing section 43 of the coupling member 40. Additionally, the joining plane 36 provided on the first face 31 of the element side substrate 30 is joined and fixed to the joining surface of the flat section 41 of the coupling member 40 with the solder. As a result, a maximum height dimension H1 of the coupled portion 48B, which is a distance from the outermost portion on the first face side of the fixing section 43 to the outermost portion of the detachable connector 34, can be expressed as $H1=H43/2+T/2+H34.$ Here, comparing H0 with H1 results in $$H1 - H0 = (H43/2 + T/2 + H34) - (L47ab + T + H34)$$
$$= H43/2 - T/2 - L47ab.$$

In the above description, since the relationship of L47*ab*<H43/2−T/2 is specified in advance, H1>H0 is obtained.

That is, the maximum height dimension H0 of the state that substrate longitudinal direction central axis 30*o* is displaced from the cable central axis 90 by the distance L can be made to be smaller than the maximum height dimension H1 of the state that the substrate longitudinal direction central axis 30*o* is matched with the cable central axis 9*o*.

Note that, in the above-described embodiment, the fixing section 43 is crimped and fixed to the cable end portion 9*r*, at which the cable general shield 9*s* is gathered, to cause the cable general shield 9*s* of the first signal cable 9*a* to come into conduction with the coupling member 40. The cable general shield 9*s* may be however joined to the coupling member 40 with solder for the conduction.

In addition, when the fixing section 43 is crimped and fixed to the cable end portion 9*r*, a heat shrinkable tube may be disposed between the outer circumferential face of the cable end portion 9*r* and the inner circumferential face of the fixing section 43, and the fixing section 43 may be crimped and fixed to the cable end portion 9*r* in the disposed state. The crimping in the state that the heat shrinkable tube is disposed can reduce the variations of crimp fixing strength.

Here, an image pickup apparatus module assembling step will be described, the image pickup apparatus module assembling step being the step of inserting the image pickup apparatus module 9S formed by integrally fixing the element side substrate 30 and the first signal cable 9*a* with the coupling member 40 into a hose 2S forming the insertion portion 2.

To form the endoscope 1, the first signal cable 9*a* extended from the image pickup apparatus 9 of the image pickup apparatus module 9S formed as described above and the element side substrate 30 provided on the cable end portion 9*r* are inserted into and caused to pass through a hose forming the insertion portion 2. The element side substrate 30 is electrically connected to the relay circuit substrate 22 arranged in the operation portion 3.

When the element side substrate 30 and the first signal cable 9*a* and the like are inserted into and caused to pass through the hose 2S as described above, static electricity is conducted, for example, to the image pickup device of the image pickup apparatus 9 through the signal lines 47 or the like, which may cause electrostatic discharge damage to the image pickup device.

Figure 11A:
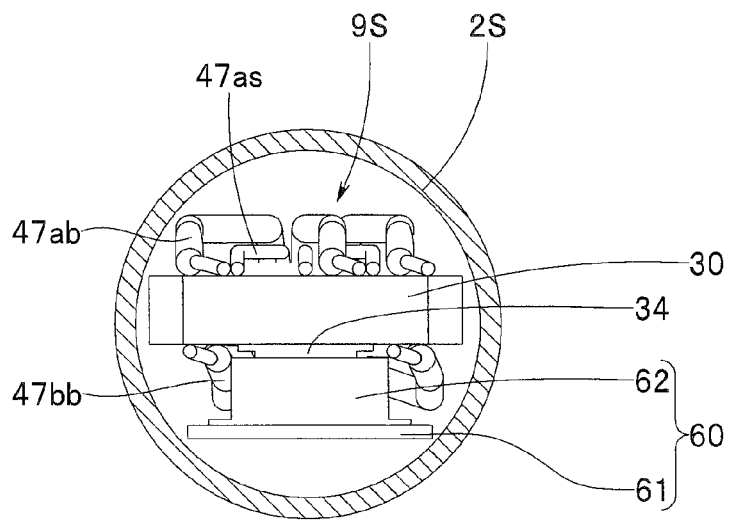
FIG. 11A is a diagram illustrating a state that a potential equalization connector having a conventional configuration is connected to the element side substrate that is integrally fixed to the first signal cable with the coupling member.

For this reason, when conducting work to insert the image pickup apparatus module 9S into the hose 2S, the operator connects a potential equalization connector 60 to the detachable connector 34, as shown in FIG. 11A, to equalize the potentials of all the signal lines, which prevents the electrostatic discharge damage to the image pickup device.

The conventional potential equalization connector 60 is however formed by installing a connection connector 62 on a thin substrate 61, taking the insertability into the hose 2S into consideration. For this reason, if the thin substrate 61 is bent when the potential equalization connector 60 is removed from the detachable connector 34, a defect occurs in which the installed connection connector 62 is detached from the thin substrate 61. The detachment of the connection connector 62 from the thin substrate 61 makes the potential equalization connector 60 unable to be reused.

Figure 11B:
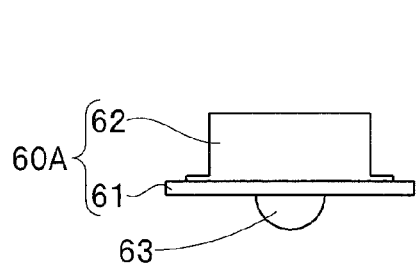
FIG. 11B is a diagram illustrating a potential equalization connector including a reinforcing portion.
Figure 11C:
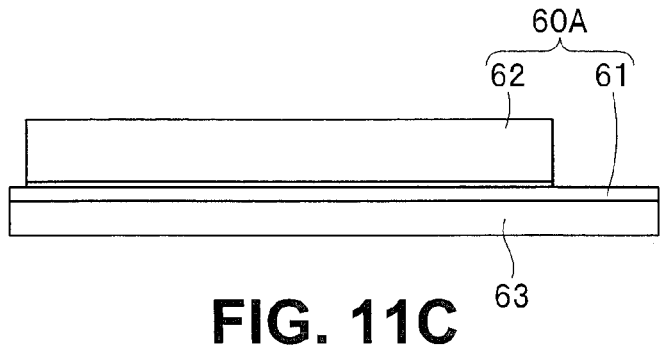
FIG. 11C is a diagram illustrating the potential equalization connector including the reinforcing portion.

To resolve this defect, a potential equalization connector 60A shown in FIG. 11B and FIG. 11C is made to be detachable from the detachable connector 34 provided on the element side substrate 30 of the image pickup apparatus module 9S in the invention of the application.

As shown in FIG. 11B and FIG. 11C, the potential equalization connector 60A is mainly formed by a reinforcing-portion-attached thin substrate 61A and the connection connector 62. The reinforcing-portion-attached thin substrate 61A is formed by providing a reinforcing portion 63 on the thin substrate 61 integrally. The reinforcing portion 63 reinforces the strength of the thin substrate 61 without reducing the hose insertability of the image pickup apparatus module 9S to which the potential equalization connector 60A is connected.

In the present embodiment, on one face side of the reinforcing-portion-attached thin substrate 61A, an electric circuit is formed on which the connection connector 62 is to be installed. The reinforcing portion 63 is provided at the longitudinal center on the other face side, shown in FIG. 11B, being the opposite face of the one face. The reinforcing portion 63 is formed by depositing solder, and made to have a cross-sectional shape that is substantially semicircular.

In addition, the reinforcing portion 63 is provided from the distal end to the proximal end of the reinforcing-portion-attached thin substrate 61A, as shown in FIG. 11C.

Figure 11D:
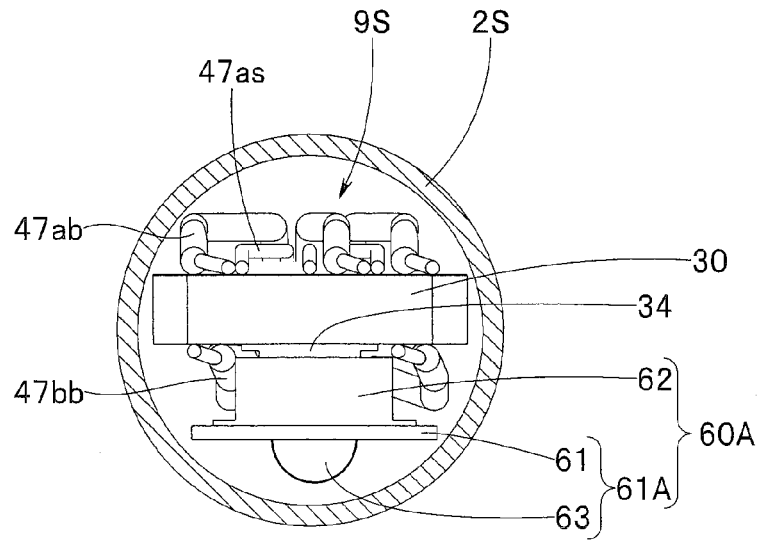
FIG. 11D is a diagram illustrating a state that the potential equalization connector including the reinforcing portion is connected to the element side substrate that is integrally fixed to the first signal cable with the coupling member.

When the image pickup apparatus module 9S in the invention of the application is inserted into the hose 2S, the potential equalization connector 60A is connected to the detachable connector 34 provided on the element side substrate 30, as shown in FIG. 11D.

As a result, in the image pickup apparatus module assembling step of inserting the first signal cable 9a including the element side substrate 30 into the hose 2S, it is possible to protect the image pickup device against the electrostatic discharge damage without reducing the inserting workability.

In addition, when the potential equalization connector 60A is removed from the detachable connector 34, the reinforcing-portion-attached thin substrate 61A is prevented from being bent. As a result, the defect in which the connection connector 62 is detached from the reinforcing-portion-attached thin substrate 61A is resolved, and the potential equalization connector 60A is enabled to be repeatedly used.

Figure 11E:
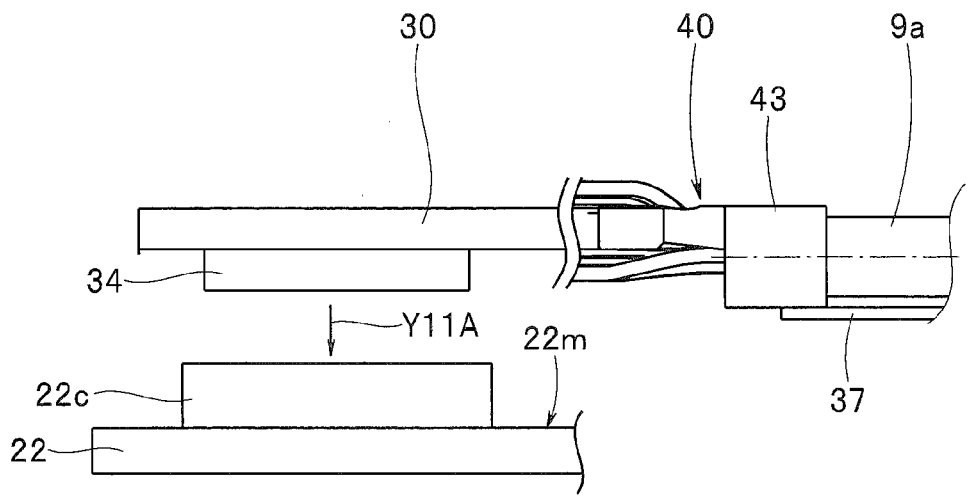
FIG. 11E is a diagram illustrating a difference in a moving direction when a detachable connector is connected on the installation face of a circuit substrate.

Then, the detachable connector 34 of the element side substrate 30, provided on the cable end portion 9r of the first signal cable 9a that passes through the hose 2S, is moved in a direction orthogonal to an installation face 22m of the relay circuit substrate 22 as shown by an arrow Y11A in FIG. 11E, and connected to a connector 22c of the relay circuit substrate 22 to which the second signal cable 9b is connected.

Reference numeral 37 denotes a jumper wire. One end portion of the jumper wire 37 is electrically connected to, for example, the outer circumferential face or the proximal end face of the fixing section 43 of the coupling member 40 connected to the element side substrate 30, and is provided being extended parallel to the signal cable 9a along a predetermined length from the end face of the fixing section 43. The other end portion of the jumper wire 37 is to be connected to the ground plane 28.

Figure 11F:
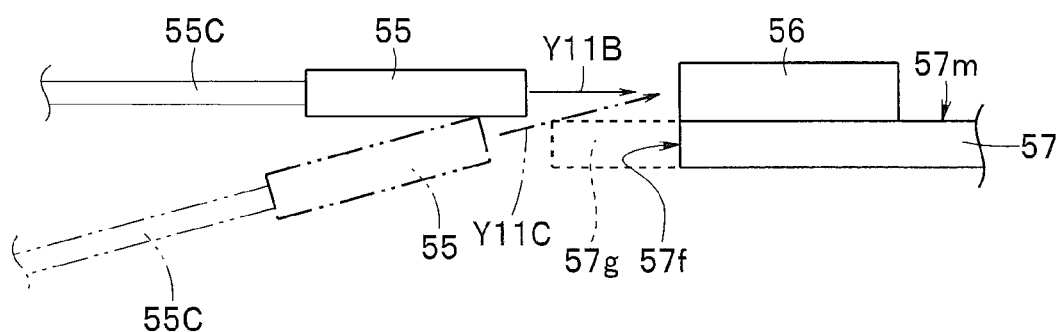
FIG. 11F is a diagram illustrating the difference in the moving direction when the detachable connector is connected on the installation face of the circuit substrate.

Note that connector connections includes a type in which the detachable connector 34 shown in FIG. 11E is moved in the direction orthogonal to the installation face 22m of the relay circuit substrate 22, and a type in which a detachable connector 55 is moved parallel to an installation face 57m of a circuit substrate 57 shown by an arrow Y11B to be connected to a connector 56 (hereafter, described as a receptacle 56) as shown in FIG. 11F. Reference character 55C denotes a signal cable, which is extended from the detachable connector 55.

In the type in which the detachable connector 55 is moved parallel to the installation face 57m to be subjected to the connector connection, if one face of the receptacle 56 and an end face 57f of the circuit substrate 57 are installed so as to match with each other, there is a risk of mistakenly moving the detachable connector 55 from below in an oblique direction with respect to the installation face 57m shown by an arrow Y11C in a chain double-dashed line, to make the connection.

Then, if the detachable connector 55 is moved from below in the oblique direction to perform the connecting operation, the receptacle 56 will be broken.

Figure 11G:
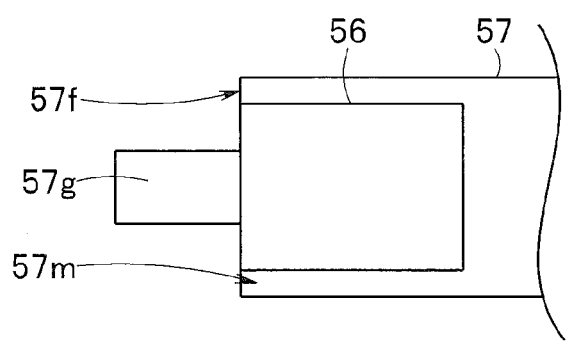
FIG. 11G is a diagram illustrating the difference in the moving direction when the detachable connector is connected on the installation face of the circuit substrate.

For this reason, in the type in which the detachable connector 55 is moved parallel to the installation face 57m to make the connector connection, as shown in FIG. 11G, a parallel movement guide portion 57g is provided on the side of the end face 57f of the circuit substrate 57. The parallel movement guide portion 57g is a projection projecting from the end face 57f of the circuit substrate 57 and provided on at least a portion of the end face 57f.

As a result of providing the parallel movement guide portion 57g on the circuit substrate 57, it is ensured that the parallel movement guide portion 57g shown in FIG. 11G prevents the connector connection from below in the oblique direction. That is, the detachable connector 55 is parallelly moved along a face on the side of the installation face 57m of the parallel movement guide portion 57g and connected to the receptacle 56.

Now, an electric circuit substrate including a heating element installed thereon needs to dissipate heat generated from the substrate. However, if a complex heat dissipation mechanism is provided in a product to dissipate the heat generated from the electric circuit substrate, disadvantages arise such as increasing the size of the apparatus, complicating the configuration of the apparatus, and increasing the cost of the apparatus.

Figure 12A:
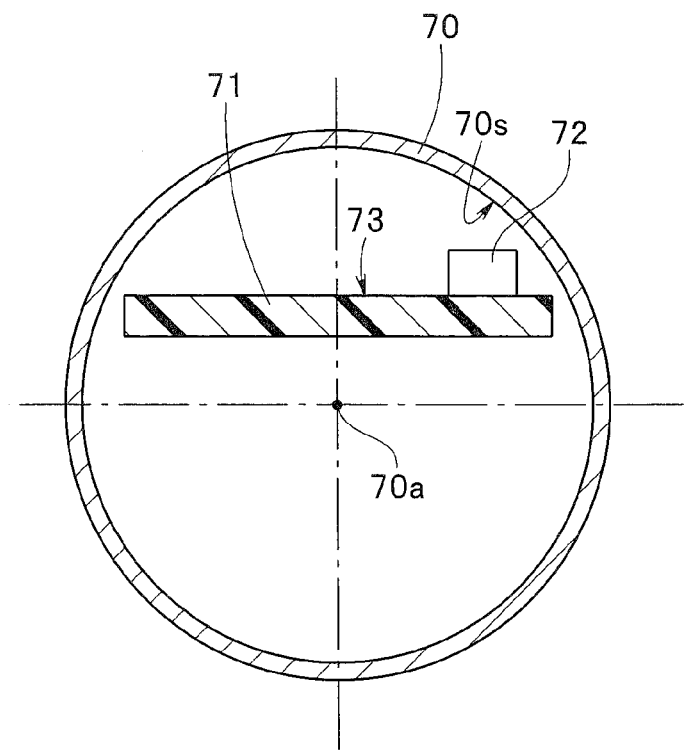
FIG. 12A is a diagram illustrating a heat dissipation structure that dissipates heat generated from an electric circuit substrate provided in an annular housing to the outside through the housing.
Figure 12B:
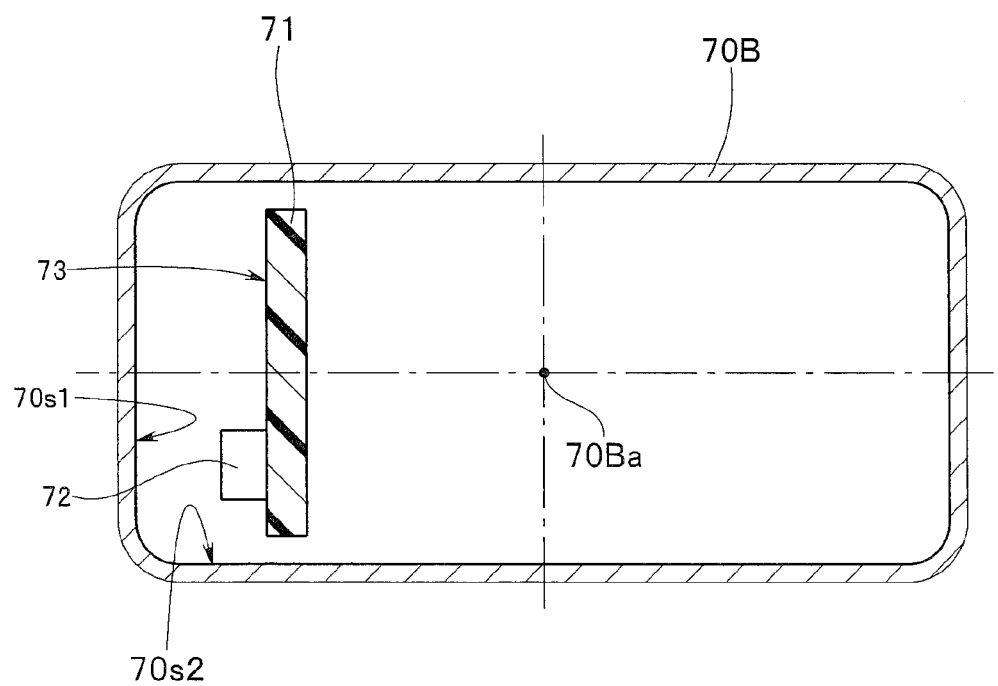
FIG. 12B is a diagram illustrating a heat dissipation structure that dissipates heat generated from an electric circuit substrate provided in a square housing to the outside through the housing.

For this reason, in the case where an electric circuit substrate is disposed in a housing such as the endoscope operation portion, the endoscope connector, and an endoscope external device, a disposed position for the electric circuit substrate is set as shown in FIG. 12A and FIG. 12B.

More specifically, in the case where the housing is an annular housing 70 configured to have, for example, a circular cross-sectional shape as shown in FIG. 12A, an electric circuit substrate 71 is disposed being displaced from a central axis 70a of the housing 70. At this point, an element 72 that generates heat the most is disposed at a position in proximity to a housing inner circumferential face 70s, on an outside face 73 that is one of the faces of the electric circuit substrate 71 and is a face opposite to a face on the side facing the central axis 70a.

As a result, the heat generated from the element 72 is conducted to the housing 70 and dissipated to the outside through the housing 70. Accordingly, the heat generated from the electric circuit substrate 71 is naturally dissipated efficiently.

As shown in FIG. 12B, in the case where the housing is, for example, a square housing 70B formed to have a rectangle cross-sectional shape, the electric circuit substrate 71 is disposed being displaced from a center 70Ba of the housing 70B. Then, the element 72 that generates heat the most is disposed at a position in proximity to, for example, a first housing inner face 70s1 and in proximity to a second housing inner face 70s2, on the outside face 73 of the electric circuit substrate 71.

As a result, the heat generated from the element 72 is conducted to the housing 70B and dissipated to the outside through the housing 70B. Accordingly, as described above, the heat generated from the electric circuit substrate 71 is naturally dissipated efficiently.

Figure 13A:
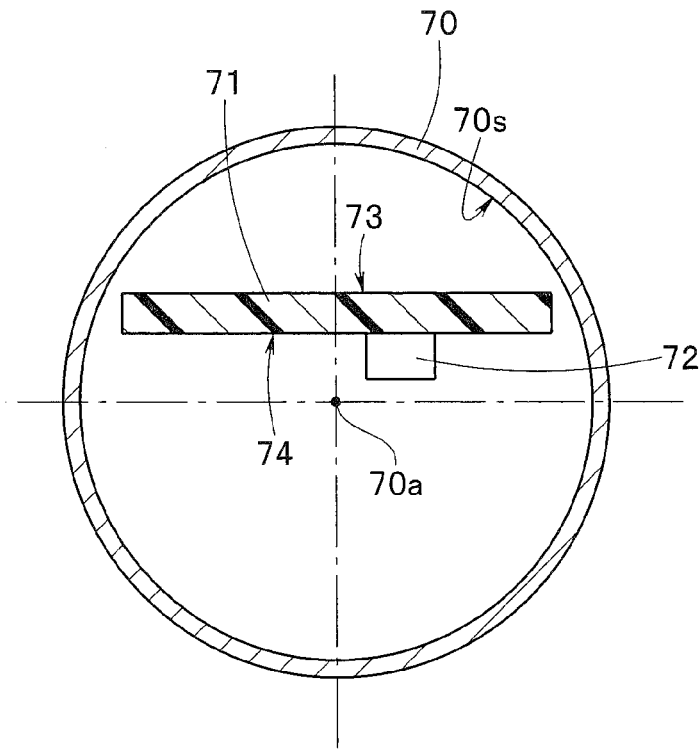
FIG. 13A is a diagram illustrating a heat dissipation structure that dissipates heat generated from the electric circuit substrate provided in the annular housing while preventing the temperature of the housing from increasing owing to the heat.
Figure 13B:
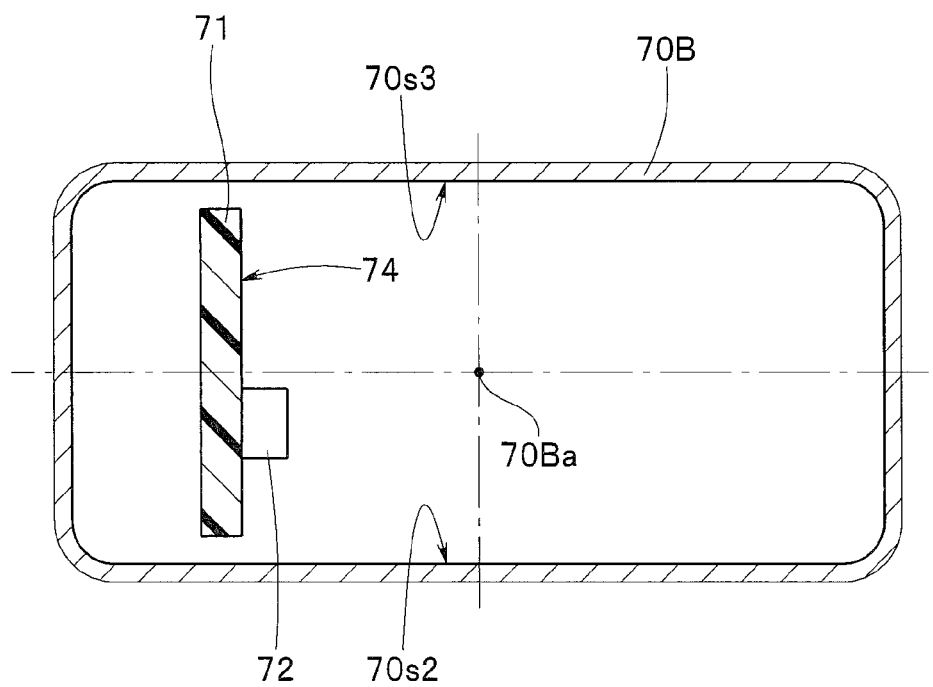
FIG. 13B is a diagram illustrating a heat dissipation structure that dissipates heat generated from the electric circuit substrate provided in the square housing while preventing the temperature of the housing from increasing owing to the heat.

Note that if the temperatures of the housings 70 and 70B increase by dissipating the heat generated from the electric circuit substrate 71 to the outside through the housings 70 and 70B as described above, which raises a disadvantage, the disposed positions of the electric circuit substrates in the housings 70 and 70B are set as shown in FIG. 13A and FIG. 13B.

When the housing is the annular housing 70, the electric circuit substrate 71 is disposed on the side of the central axis 70a of the housing 70, or the electric circuit substrate 71 is disposed being displaced from the central axis 70a of the housing 70, as shown in FIG. 13A. Then, the element 72 that generates heat the most is disposed at a position away from the housing inner circumferential face 70s of the annular housing 70, on an inner side face 74 that is one of the faces of the electric circuit substrate 71 and is a face on a side facing the central axis 70a.

As a result, the heat generated from the element 72 is dissipated to the internal space of the housing 70 and afterward conducted to the housing 70. Accordingly, the temperature of the housing 70 is prevented from increasing owing to the heat dissipated from the electric circuit substrate 71.

As shown in FIG. 13B, when the housing is the square housing 70B, the electric circuit substrate 71 is disposed being displaced from the center 70Ba of the housing 70B. Then, the element 72 that generates heat the most is disposed at a position away from the second housing inner face 70s2 or a third housing inner face 70s3, on the inner side face 74 of the electric circuit substrate 71.

As a result, the heat generated from the element 72 is dissipated to the internal space of the housing 70 and afterward conducted to the housing 70. Accordingly, as described above, the temperature of the housing 70 is prevented from increasing owing to the heat dissipated from the electric circuit substrate 71.

Figure 14A:
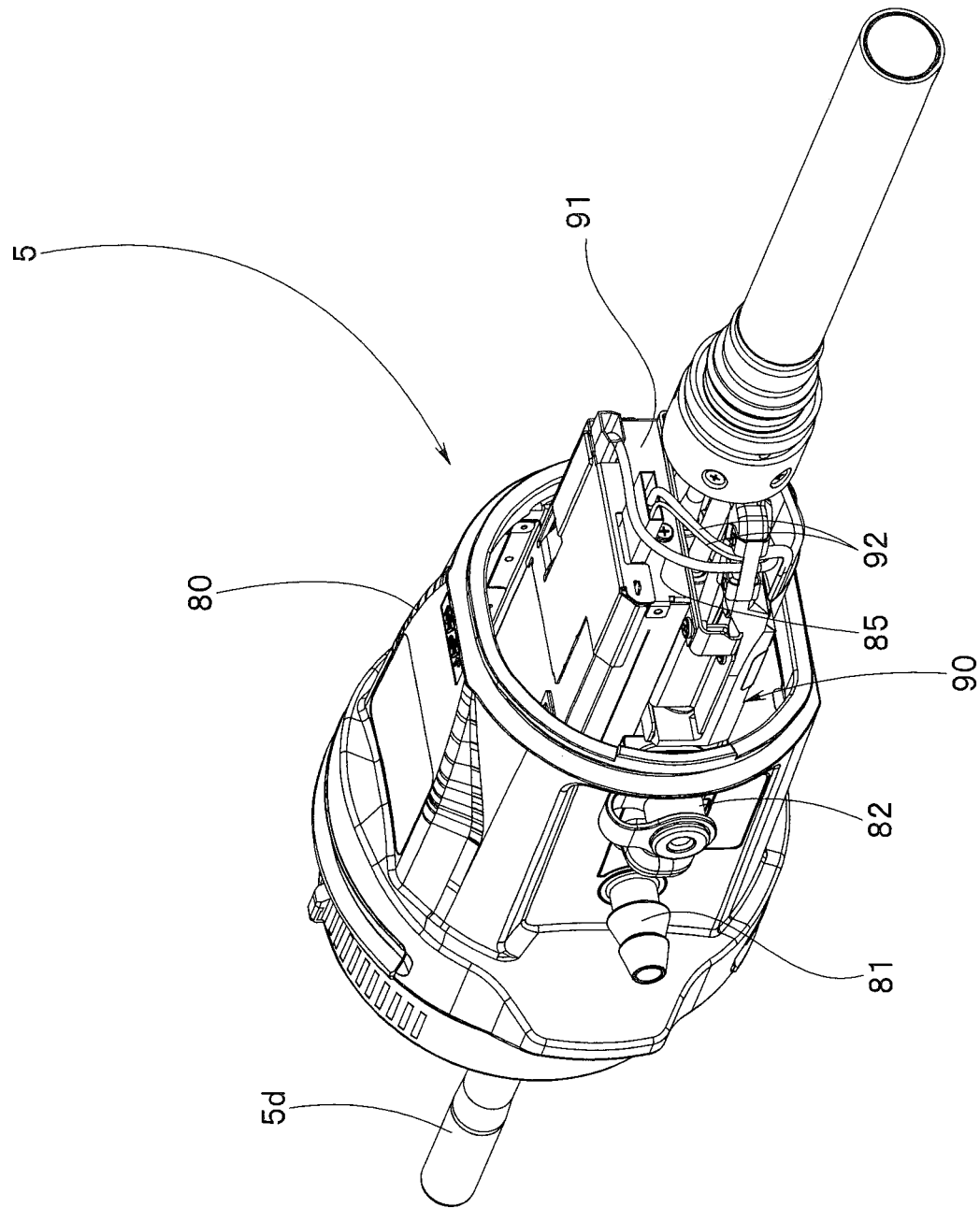
FIG. 14A is a diagram illustrating the endoscope connector from which a first unit is removed.
Figure 14B:
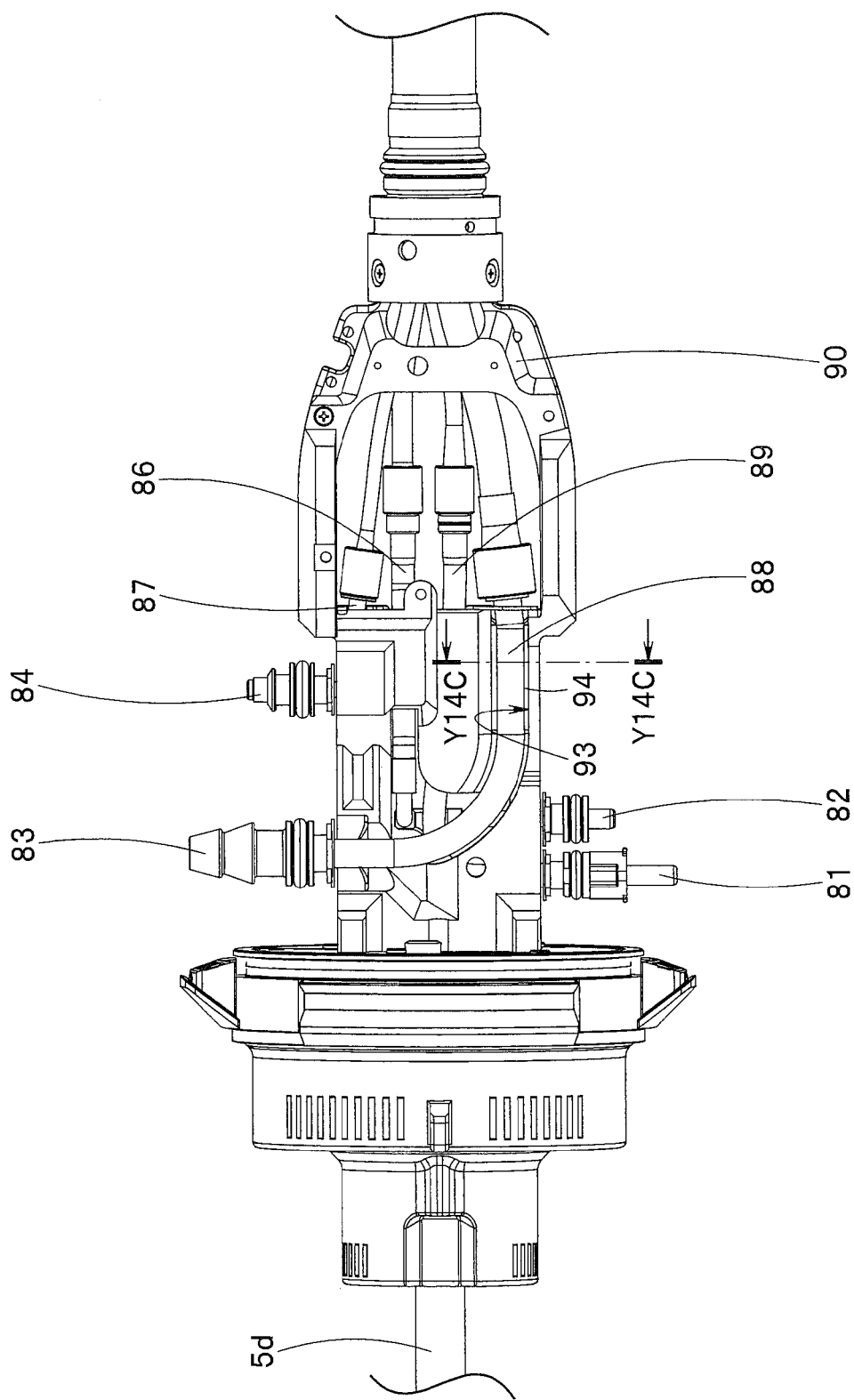
FIG. 14B is a diagram illustrating the relationship among various pipe sleeves provided in the endoscope connector, various conduits, and a main frame.
Figure 14C:
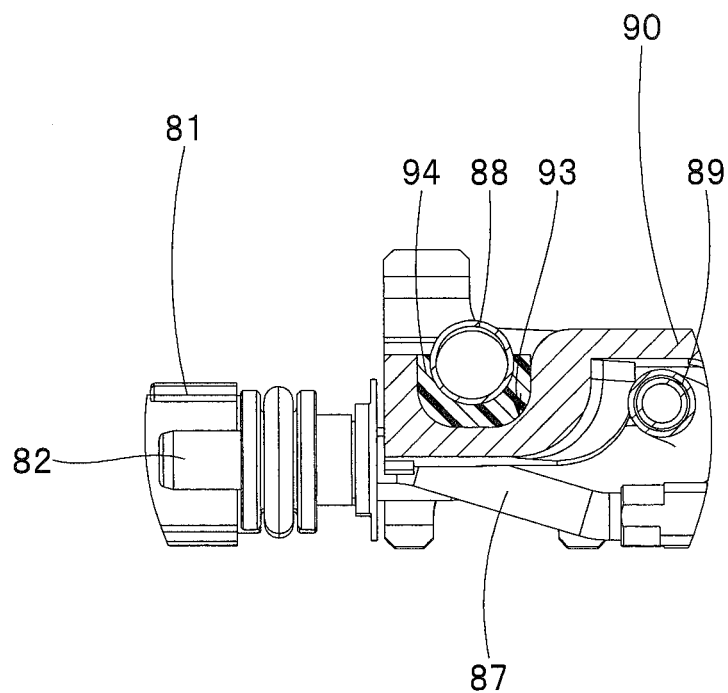
FIG. 14C is a cross sectional view taken along the line Y14C-Y14C of FIG. 14B, being a diagram illustrating a configuration that forcibly dissipates heat generated in the electric circuit substrate through fluid.

Now, in the endoscope connector, in the case where the electric circuit substrate generating heat is disposed in the connector, employing configurations shown in FIG. 14A to FIG. 14C allows the heat generated from the electric circuit substrate to be forcibly dissipated through fluid.

As shown in FIG. 14A and FIG. 14B, the endoscope connector 5 includes a first exterior unit (not shown) that is integrally provided in the proximal end portion of the universal cable 4, and a second exterior unit 80 forming a connector proximal end side. From the proximal end face of the second exterior unit 80, a light guide pipe sleeve (reference character 5c in FIG. 2) and an air feeding pipe sleeve 5d project.

In addition, in the side portions of the second exterior unit 80, a water feeding pipe sleeve 81, a pressurizing pipe sleeve 82, a suction pipe sleeve 83, and a forward tank element pipe sleeve 84 are provided.

In the internal space of the endoscope connector 5, a light guide fiber bundle 85 is provided, as well as a water feeding conduit 86, a pressurizing conduit 87, a suction conduit 88, a sub water feeding conduit 89 the end portions of which the various pipe sleeves 81, 82, 83, and 84 are connected, a main frame 90, a circuit substrate 91, a signal line 92, and the like. On one face of the main frame 90, a suction conduit disposing groove 93 is formed that is used for disposing and guiding, for example, the suction conduit 88. Then, as shown in FIG. 14C, a heat dissipation sheet 94 is provided between the suction conduit disposing groove 93 and the suction conduit 88. One face side of the heat dissipation sheet 94 is in close contact with the suction conduit 88, and the other face side is in close contact with the suction conduit disposing groove 93. In addition, on one side of the main frame 90, the circuit substrate 91 is placed and arranged.

Note that, in the above-described embodiment, it is assumed that the heat dissipation sheet 94 is provided between the suction conduit disposing groove 93 and the suction conduit 88. The heat dissipation sheets 94 are however provided between a water feeding conduit disposing groove and the water feeding conduit 86, between a pressurizing conduit disposing groove and the pressurizing conduit 87, and between a sub water feeding conduit disposing groove and the sub water feeding conduit 89, although not shown.

As seen from the above, providing the heat dissipation sheets between the individual conduit disposing grooves and the respective conduits causes heat generated from the circuit substrate 91 to be conducted to the main frame 90, conducted afterward through the heat dissipation sheets 94 arranged in the respective conduit disposing grooves and the various conduits 86, 87, 88, and 89, and dissipated into fluid such as water and air passing through the various conduits 86, 87, 88, and 89. Accordingly, the heat generated from the circuit substrate 91 can be forcibly dissipated through the fluid passing through the conduits 86, 87, 88, and 89.

Now, the endoscope 1 may include in the endoscope connector 5 an RFID that communicates with the external device. The RFID includes a storage section in which reprocess information, endoscope internal information, and the like are stored, a communication processing device that performs communication, an antenna, and the like.

The antenna of the RFID typically performs communication in one direction by specification. For this reason, the change in a communication direction disables the communication, which makes the RFID unable to give and receive information.

The endoscope connector 5 shown in FIG. 15A includes an RFID 100 that can perform communication in two directions.

Figure 15B:
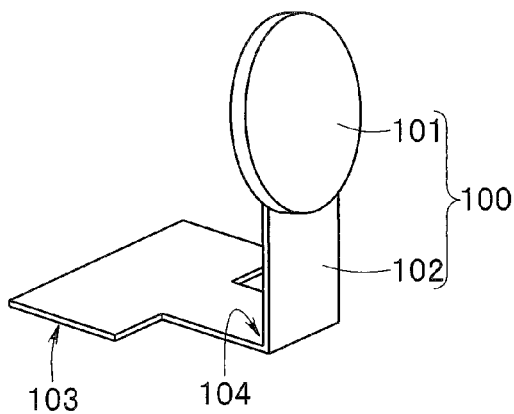
FIG. 15B is a diagram illustrating a configuration example of the RFID that can perform communication in two directions.

The RFID 100 shown in FIG. 15B includes an RFID main body 101 and a flexible printed circuit 102. The RFID main body 101 is provided with a storage section, a communication processing device, an antenna, and the like. The flexible printed circuit 102 has one end portion connected to the RFID main body 101, and the other end portion provided with an antenna section 103 that performs communication. Then, the flexible printed circuit 102 includes a bent portion 103a, between the other end portion and the one end portion, which is bent, for example, at 90 degrees.

This configuration enables communication by the antenna of RFID main body 101 in a direction and communication by the antenna section 103 in a direction orthogonal to the direction of the communication by the antenna of the main body 101.

Note that the two communication directions are not limited to one direction and a direction orthogonal to the one direction, and communication in two predetermined directions can be performed by setting a bending angle of the bent portion 103a as appropriate.

In addition, the number of the communication directions is not limited to two, and a plurality of antenna sections 103 may be provided in the end portion of the flexible printed circuit 102 to enable communication in three directions or communication in four directions.

Figure 15C:
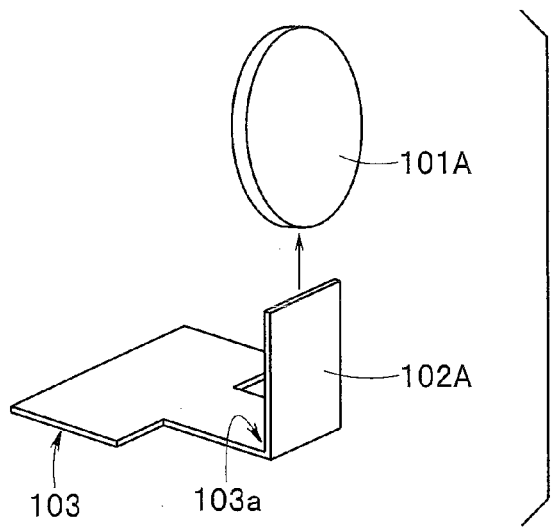
FIG. 15C is a diagram illustrating a configuration example of the RFID that can perform communication in two directions.

Furthermore, the configuration of the RFID is not limited to the RFID 100 and may be, for example, a configuration in which an RFID main body 101A is made to be detachable with respect to a flexible printed circuit 102A, as shown in FIG. 15C.

Figure 15D:
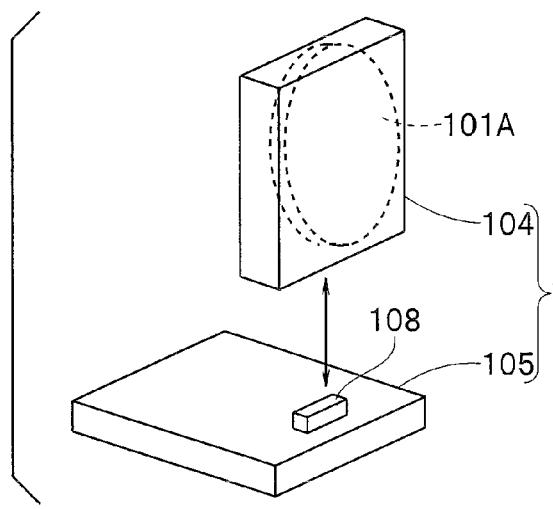
FIG. 15D is a diagram illustrating a configuration example of the RFID that can perform communication in two directions.
Figure 15E:
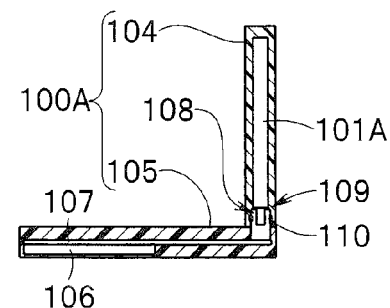
FIG. 15E is a diagram illustrating a configuration example of the RFID that can perform communication in two directions.

In addition, as shown in an exploded perspective view and an assembly cross sectional view that are shown in FIG. 15D and FIG. 15E, an RFID 100A may be formed by a first antenna apparatus 104 that incorporates the RFID main body 101A and a second antenna apparatus 105 that is detachable with respect to the first antenna apparatus 104.

The second antenna apparatus 105 includes a second antenna section 106 and an RFID main body connection portion 107, and the first antenna apparatus 104 and the second antenna apparatus 105 are configured to be detachable via a coupling portion 109 including a connector 108.

Reference numeral 110 denotes a gasket that maintains the water tightness of the first antenna apparatus 104, the second antenna apparatus 105, and the coupling portion 109.

Note that the present invention is not limited only to the above-described embodiment and various modifications are possible without departing the gist of the present invention.

What is claimed is:

1. A substrate connecting structure comprising:
   a circuit substrate including a front face and a back face opposite to the front face, where an electrical component is installed on the back face;
   a signal cable into which a plurality of signal transmission lines are inserted, the plurality of signal transmission lines being electrically connected to first signal line connecting portions provided at predetermined positions on the front face and to second signal line connecting portions provided at predetermined positions on the back face, respectively; and
   a coupling member that is formed by a conductive member including an annular fixing section disposed and fixed so as to cover and wrap an outer circumferential face of a cable end portion of the signal cable, a flat section joined and fixed to a front face of the circuit substrate, and a through hole that is provided between the flat section and the fixing section and communicates between one face and another face of the coupling member, the coupling member integrally fixing the signal cable and the circuit substrate, wherein
   a cable central axis of the signal cable fixed to the fixing section is displaced toward a side of the back face with respect to a longitudinal direction central axis of the circuit substrate to which the flat section is fixed.

2. The substrate connecting structure according to claim 1, wherein the through hole of the coupling member is a signal line insertion hole that guides a portion of signal transmission lines among the plurality of signal transmission lines inserted into the signal cable to another face of the circuit substrate to which the flat section of the coupling member is joined and fixed.

3. The substrate connecting structure according to claim 2, wherein the through hole of the coupling member forms a part of the flat section of the coupling member.

4. The substrate connecting structure according to claim 1, wherein the flat section of the coupling member is joined and fixed to a planar ground pattern provided on the circuit substrate, the planar ground pattern including at least the flat section.

5. The substrate connecting structure according to claim 4, wherein the flat section of the coupling member is joined to the ground pattern with solder.

6. The substrate connecting structure according to claim 1, wherein the fixing section of the coupling member is fixed to an outer circumference of the signal cable by being subjected to plastic deformation.

7. The substrate connecting structure according to claim 6, wherein the fixing section of the coupling member is in contact with and fixed to a shielding member that is exposed to the outer circumference of the signal cable.

8. The substrate connecting structure according to claim 1, wherein the electrical component installed on the back face of the circuit substrate is a connector, and the connector is electrically connected to another connector after the circuit substrate is inserted into a hose forming an insertion portion of an endoscope and passes through the hose, the other connector being provided in an operation portion or in an endoscope connector provided in series to the insertion portion.

9. The substrate connecting structure according to claim 8, further comprising a jumper wire at least one end of which is extended parallel to the signal cable, and the one end is connected to the coupling member.

10. The substrate connecting structure according to claim 9, wherein another end of the jumper wire is electrically connected to a member that is grounded in the operation portion or in the endoscope connector.

* * * * *